(12) United States Patent
Trull et al.

(10) Patent No.: US 11,651,051 B2
(45) Date of Patent: May 16, 2023

(54) REMOTE RESPIRATORY THERAPY DEVICE MANAGEMENT

(71) Applicant: ResMed Pty Ltd, Bella Vista (AU)

(72) Inventors: Wendall Eric Trull, San Diego, CA (US); Boris Kovtun, San Diego, CA (US); Tara Kalro, San Diego, CA (US); Joseph White, San Diego, CA (US); Chinmayee Somaiya, Sydney (AU); Amila Fernando, Pennant Hills (AU); Andrew Weale, San Diego, CA (US); Maurizio Borsotto, San Diego, CA (US)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/854,956

(22) Filed: Jun. 30, 2022

(65) Prior Publication Data

US 2022/0342957 A1    Oct. 27, 2022

Related U.S. Application Data

(63) Continuation of application No. 17/302,992, filed on May 18, 2021, now Pat. No. 11,423,119, which is a (Continued)

(51) Int. Cl.
*G06F 17/40* (2006.01)
*G06F 16/23* (2019.01)

(52) U.S. Cl.
CPC ............ *G06F 17/40* (2013.01); *G06F 16/23* (2019.01); *A61M 2205/502* (2013.01); *A61M 2205/52* (2013.01)

(58) Field of Classification Search
CPC .. G06F 17/40; G06F 16/23; A61M 2205/502; A61M 2205/52
See application file for complete search history.

(56) References Cited

U.S. PATENT DOCUMENTS

| 7,574,368 B2 | 8/2009 | Pawlikowski et al. |
| 7,913,689 B2 | 3/2011 | Henry et al. |

(Continued)

FOREIGN PATENT DOCUMENTS

| CN | 102136934 | 7/2011 |
| CN | 104834537 | 8/2015 |

(Continued)

OTHER PUBLICATIONS

International Search Report for Application No. PCT/IB2020/060711, six pages, dated Jan. 15, 2021.

(Continued)

*Primary Examiner* — Phillip H Nguyen
(74) *Attorney, Agent, or Firm* — Nixon & Vanderhye P.C.

(57) ABSTRACT

A server is provided and is programmed to automatically determine, based on the identification data that uniquely identifies a patient device, whether there is an upgrade to the code or data (e.g., software or firmware) stored in the electronic memory of the patient device that can be applied thereto. In response to determination that there is an upgrade that can be applied, a data package is delivered to the patient device via the first wireless transceiver, the data package to be automatically applied to the electronic memory of the patient device.

20 Claims, 18 Drawing Sheets

Related U.S. Application Data continuation of application No. 17/097,962, filed on Nov. 13, 2020, now Pat. No. 11,042,606.

(60) Provisional application No. 62/935,356, filed on Nov. 14, 2019.

(56) References Cited

U.S. PATENT DOCUMENTS

| | | | |
|---|---|---|---|
| 7,924,150 B2 | 4/2011 | Baldus et al. |
| 7,978,062 B2 | 7/2011 | Lalonde et al. |
| 8,058,986 B2 | 11/2011 | Klabunde et al. |
| 8,302,600 B2 | 11/2012 | Andrieux et al. |
| 8,302,602 B2 | 11/2012 | Andrieux et al. |
| 8,373,556 B2 | 2/2013 | Lalonde et al. |
| 8,395,498 B2 | 3/2013 | Gaskill et al. |
| 8,515,547 B2 | 8/2013 | Mass et al. |
| 8,587,427 B2 | 11/2013 | Lalonde et al. |
| 8,694,600 B2 | 4/2014 | Gaines et al. |
| 8,818,522 B2 | 8/2014 | Mass et al. |
| 8,863,106 B2 | 10/2014 | Schöller et al. |
| 8,943,168 B2 | 1/2015 | Wiesner et al. |
| 8,950,398 B2 | 2/2015 | Andrieux et al. |
| 8,970,392 B2 | 3/2015 | Lalonde et al. |
| 9,269,251 B2 | 2/2016 | Lalonde et al. |
| 9,289,571 B2 | 3/2016 | Peiris et al. |
| 9,495,511 B2 | 11/2016 | Harrington et al. |
| 9,848,058 B2 | 12/2017 | Johnson et al. |
| 10,108,785 B2 | 10/2018 | Kamen et al. |
| 10,255,647 B2 | 4/2019 | Rodman et al. |
| 10,290,071 B2 | 5/2019 | Heil et al. |
| 10,293,124 B2 | 5/2019 | Bychkov et al. |
| 11,042,606 B2 | 6/2021 | Trull et al. |
| 2002/0123673 A1 | 9/2002 | Webb |
| 2006/0064323 A1 | 3/2006 | Alleckson et al. |
| 2006/0189854 A1 | 8/2006 | Webb |
| 2008/0271010 A1 | 10/2008 | Scholler |
| 2009/0063193 A1 | 3/2009 | Barton et al. |
| 2009/0081951 A1 | 3/2009 | Erdmann et al. |
| 2011/0073107 A1* | 3/2011 | Rodman ................ G16H 40/63 141/2 |
| 2013/0036412 A1 | 2/2013 | Birtwhistle et al. |
| 2013/0154851 A1 | 6/2013 | Gaskill et al. |
| 2013/0239961 A1 | 9/2013 | Ross, Jr. et al. |
| 2013/0317753 A1 | 11/2013 | Kamen et al. |
| 2013/0317837 A1* | 11/2013 | Ballantyne .......... A61M 1/3627 705/2 |
| 2014/0102455 A1 | 4/2014 | D'Angelo et al. |
| 2014/0188516 A1 | 7/2014 | Kamen et al. |
| 2014/0366876 A1 | 12/2014 | Huby et al. |
| 2015/0006196 A1* | 1/2015 | Schoeller ................ G06F 8/65 705/2 |
| 2015/0070187 A1 | 3/2015 | Wiesner et al. |
| 2015/0154364 A1 | 6/2015 | Biasi et al. |
| 2015/0370551 A1 | 12/2015 | Mahajan |
| 2016/0034655 A1 | 2/2016 | Gray et al. |
| 2016/0188318 A1 | 6/2016 | Li et al. |
| 2016/0193437 A1 | 7/2016 | Bao et al. |
| 2016/0199601 A1 | 7/2016 | Peiris et al. |
| 2017/0136198 A1 | 5/2017 | Delangre et al. |
| 2017/0239432 A1 | 8/2017 | Delangre et al. |
| 2017/0242683 A1 | 8/2017 | Nekoomaram et al. |
| 2018/0233225 A1 | 8/2018 | Experton et al. |
| 2018/0286510 A1 | 10/2018 | Kwan et al. |
| 2021/0125713 A1* | 4/2021 | Audrain ............ G16H 20/17 |
| 2021/0146080 A1 | 5/2021 | Trull et al. |

FOREIGN PATENT DOCUMENTS

| | | |
|---|---|---|
| CN | 107203395 | 9/2017 |
| CN | 107358032 | 11/2017 |

OTHER PUBLICATIONS

Written Opinion of the ISA for Application No. PCT/IB2020/060711, six pages, dated Jan. 15, 2021.
Notification of the First Office Action with English Translation for Chinese Application No. 202080086564.5, 20 pages, dated Dec. 28, 2022.

* cited by examiner

REMOTE RESPIRATORY THERAPY DEVICE MANAGEMENT

1 CROSS-REFERENCE TO RELATED APPLICATIONS

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

This application is a Continuation of U.S. patent application Ser. No. 17/302,992, filed May 18, 2021, now allowed; which is a Continuation of U.S. patent application Ser. No. 17/097,962, filed Nov. 13, 2020, now U.S. Pat. No. 11,042,606, issued Jun. 22, 2021; which claims the benefit of Provisional Application No. 62/935,356, filed Nov. 14, 2019; the entire contents being incorporated herein. The contents of U.S. Publication No. 2017/0136198 is incorporated herein by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use. The present technology relates to medical devices or apparatus, their use, and updating the same.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O. For flow therapies such as nasal HFT, the patient interface is configured to insufflate the nares but specifically to avoid a complete seal. One example of such a patient interface is a nasal cannula.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator. RPT devices have also been known as flow generators.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

2.2.3.5 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

An aspect of certain forms of the present technology is to provide methods and/or apparatus that improve the compliance of patients with respiratory therapy.

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

One form of the present technology comprises techniques for automatically managing and maintaining updates (e.g., software, settings, firmware, etc.) to multiple diverse patient devices.

Another aspect of one form of the present technology is the use of rule-based processing that responds to individually submitted requests from patient devices that included identification data associated with the specific device. Such information allows a system to automatically determine what updates to apply to the patient device without having to manually trigger such updates.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring, and/or treatment of respiratory conditions, including, devices that provide monitoring and/or treatment of, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

4.3 Patient Interface

FIG. 3A shows a patient interface in the form of a nasal mask in accordance with one form of the present technology.

4.4 RPT Device

4.5 Humidifier

Figure 5A:
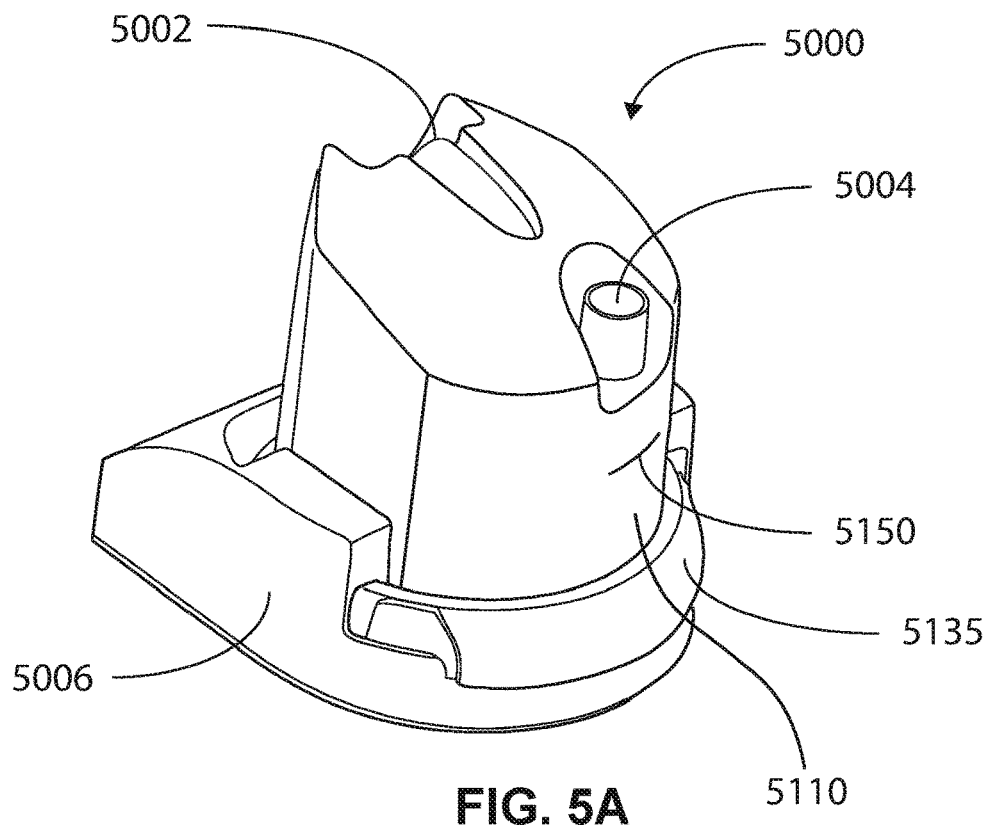

FIG. 5A shows an isometric view of a humidifier in accordance with one form of the present technology.

Figure 5B:
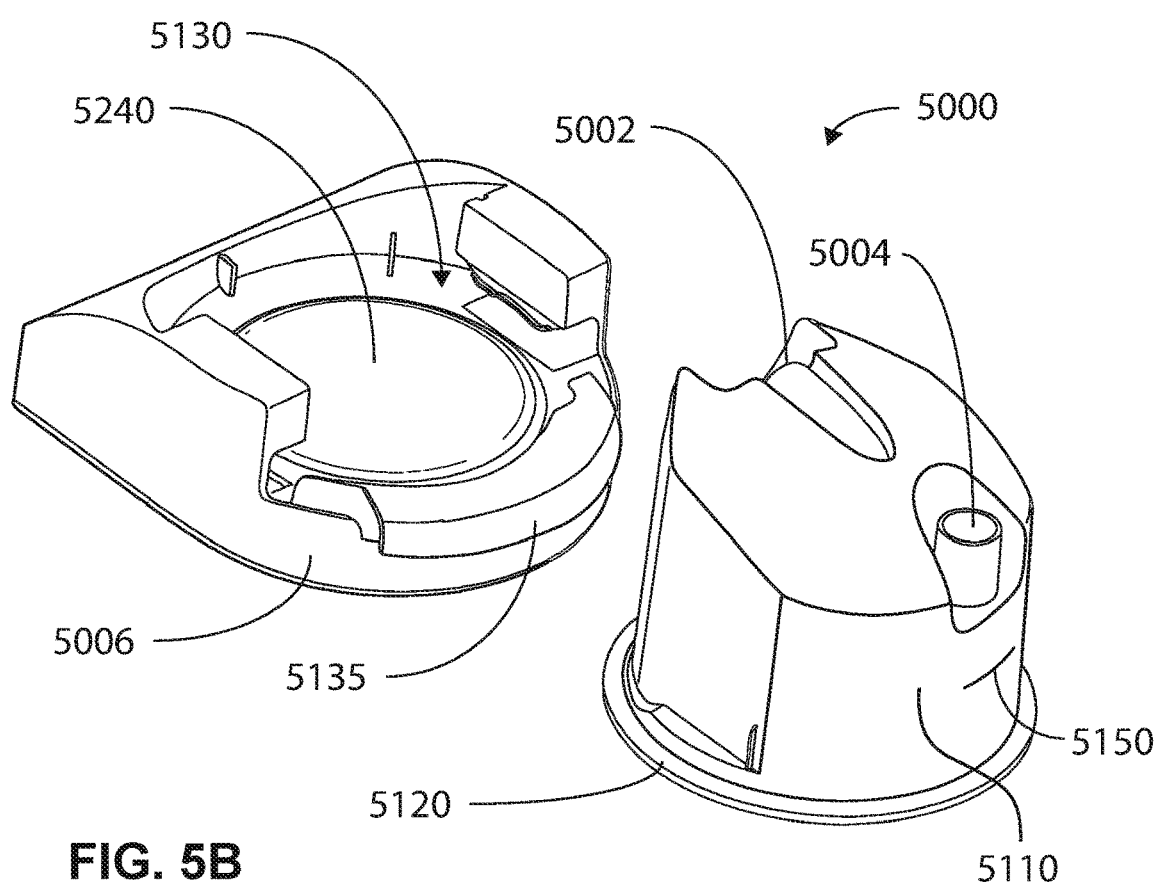

FIG. 5B shows an isometric view of a humidifier in accordance with one form of the present technology, showing a humidifier reservoir 5110 removed from the humidifier reservoir dock 5130.

4.6 Breathing Waveforms

Figure 6A:
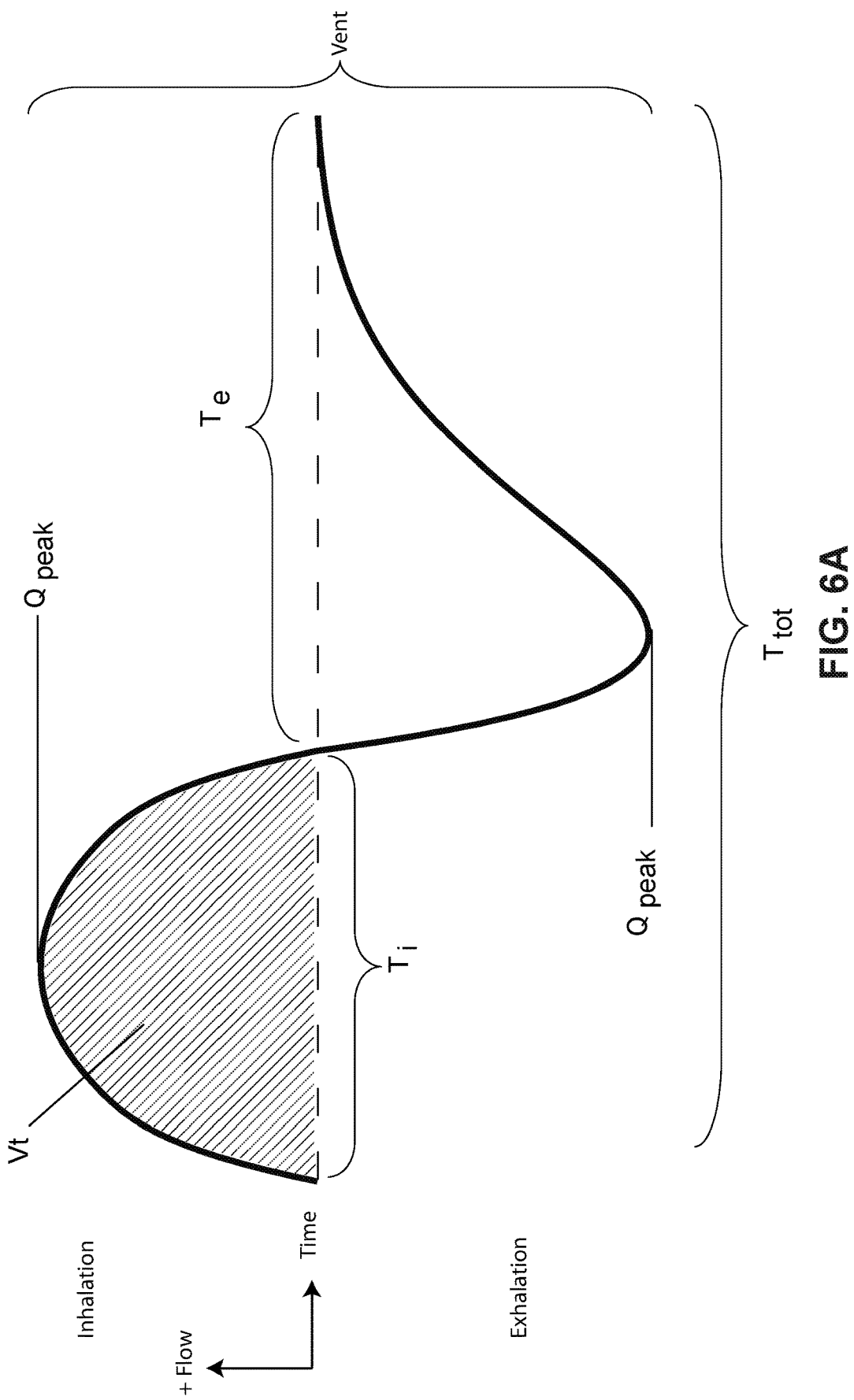

FIG. 6A shows a model typical breath waveform of a person while sleeping.

4.7 Data Management System

Figure 7:
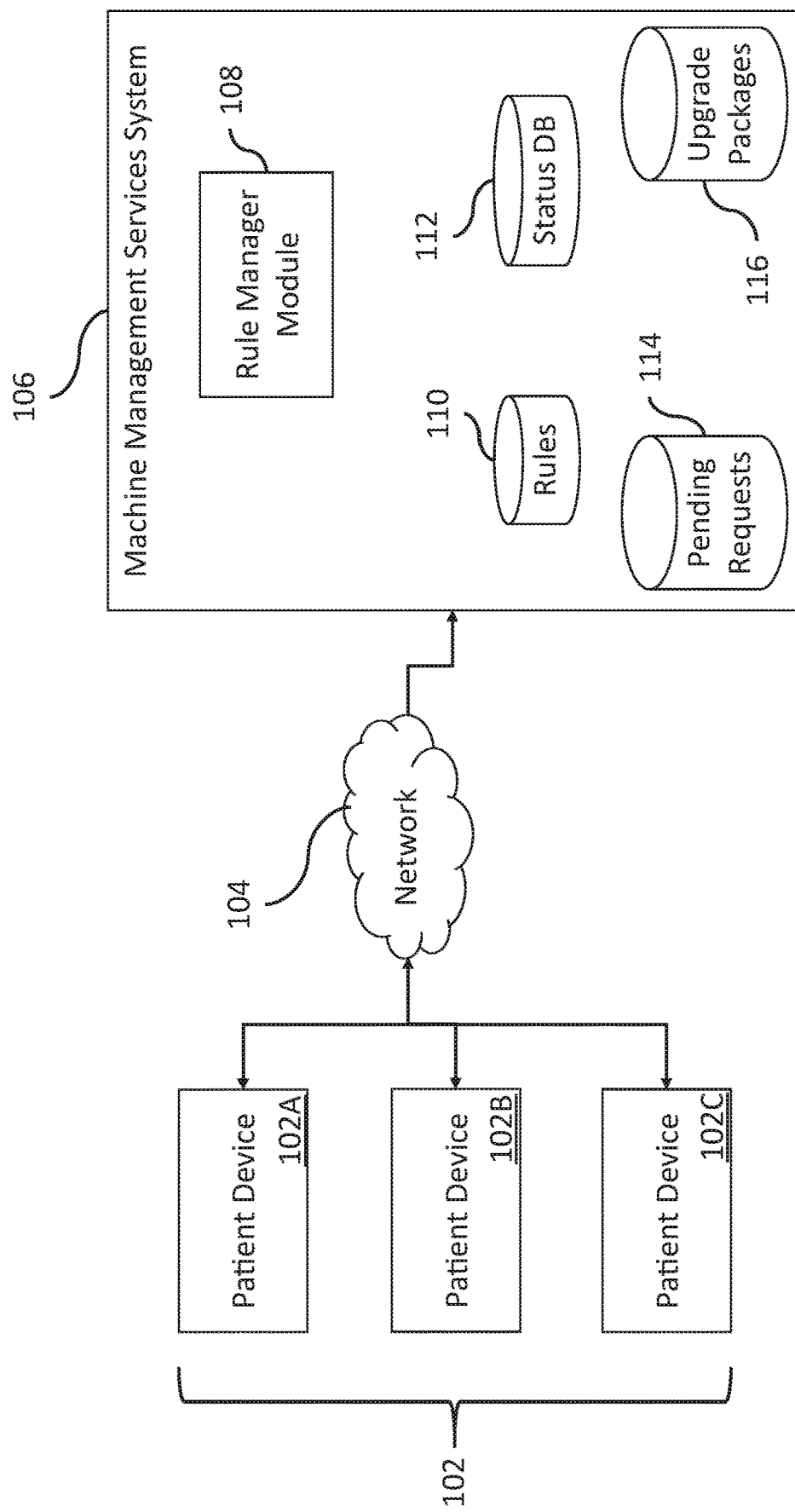

FIG. 7 shows an example Machine Management Services System 106 that is used to communicate with, and provide updates to, patient devices 102 (102A, 102B, 102C) in accordance with certain examples.

Figure 8:
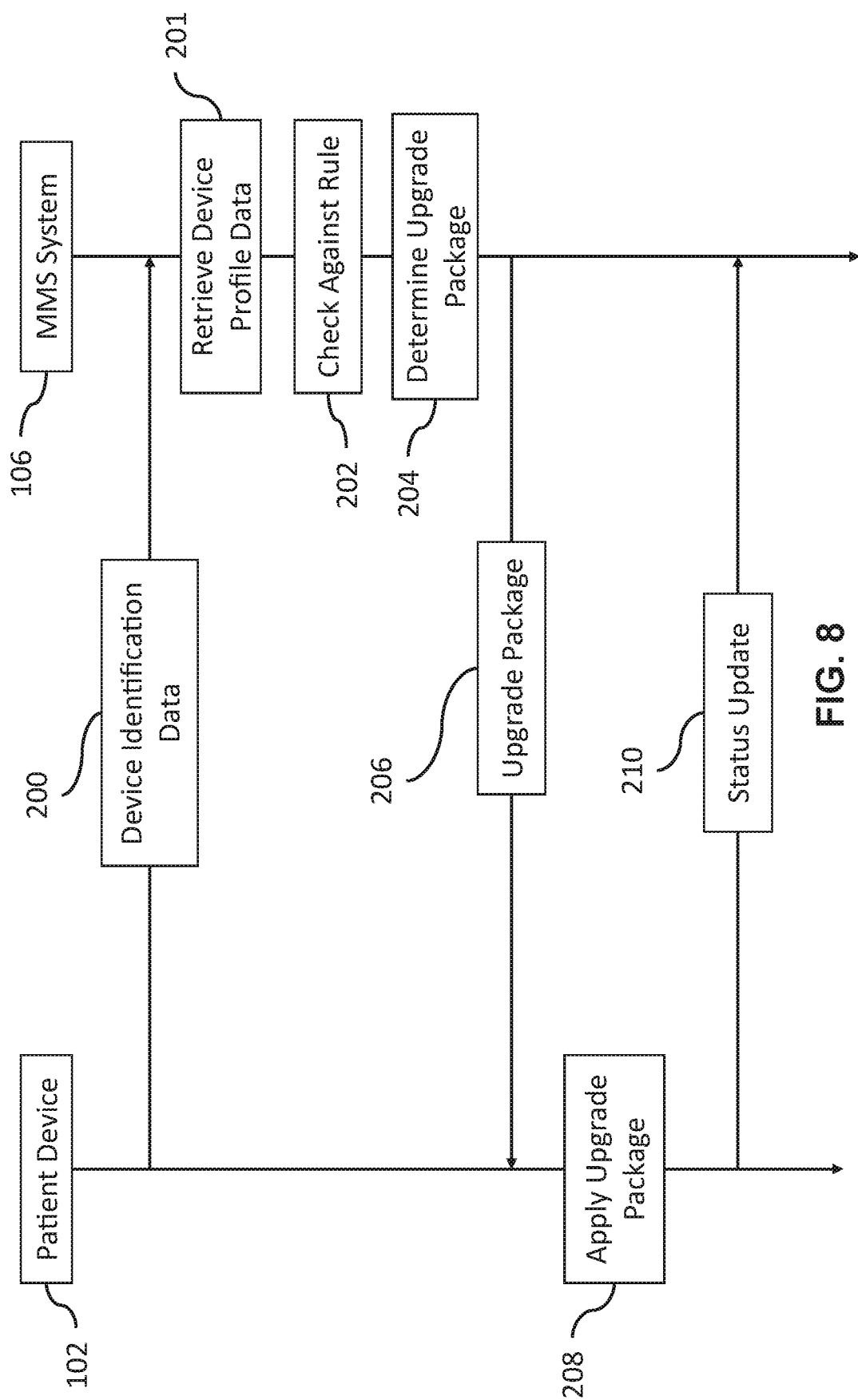

FIG. 8 shows a signal diagram that shows communications between an example RPT device and the example Machine Management Services System of FIG. 7.

Figure 9A:
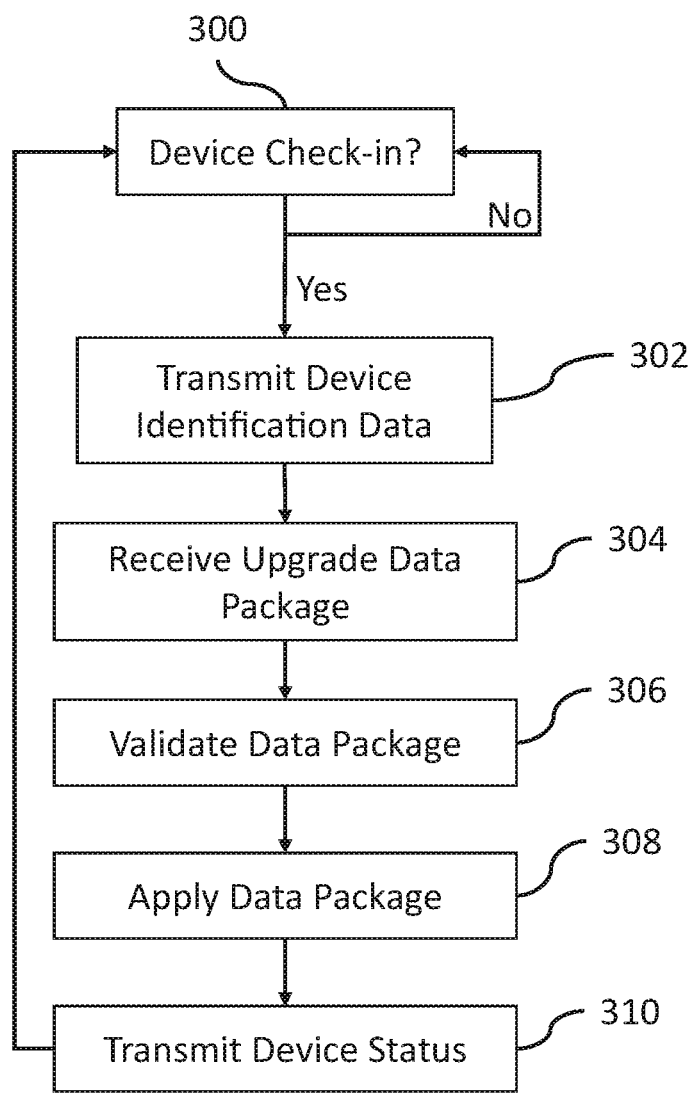
Figure 9B:
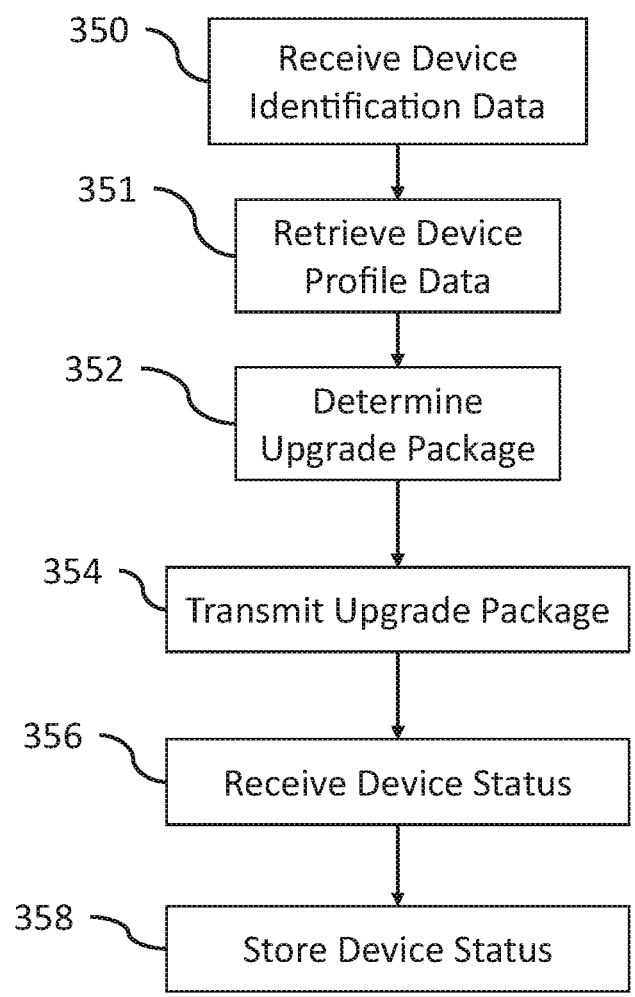

FIGS. 9A and 9B are flow chart of computer operations that may be executed in certain examples.

Figure 10A:
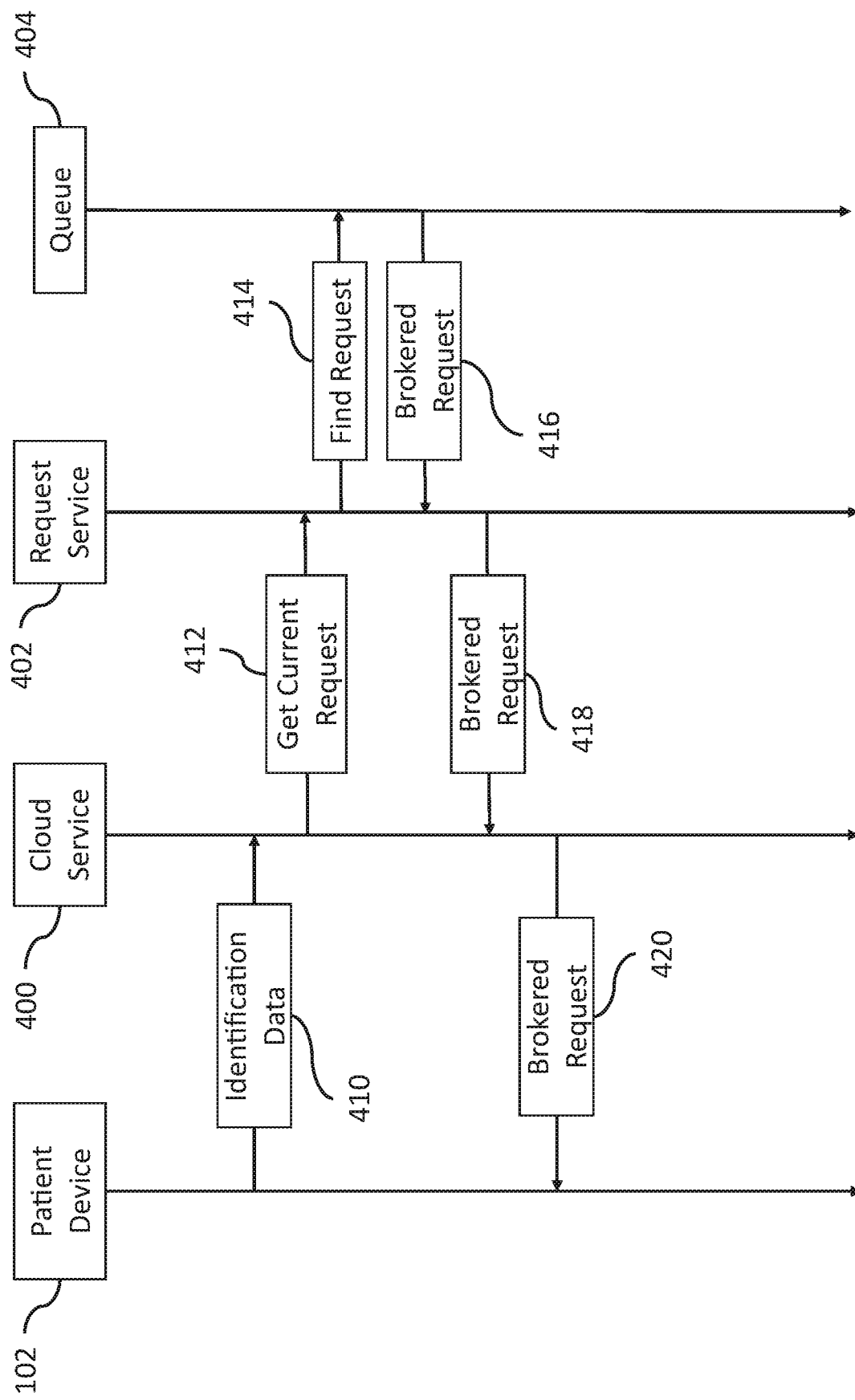
Figure 10B:
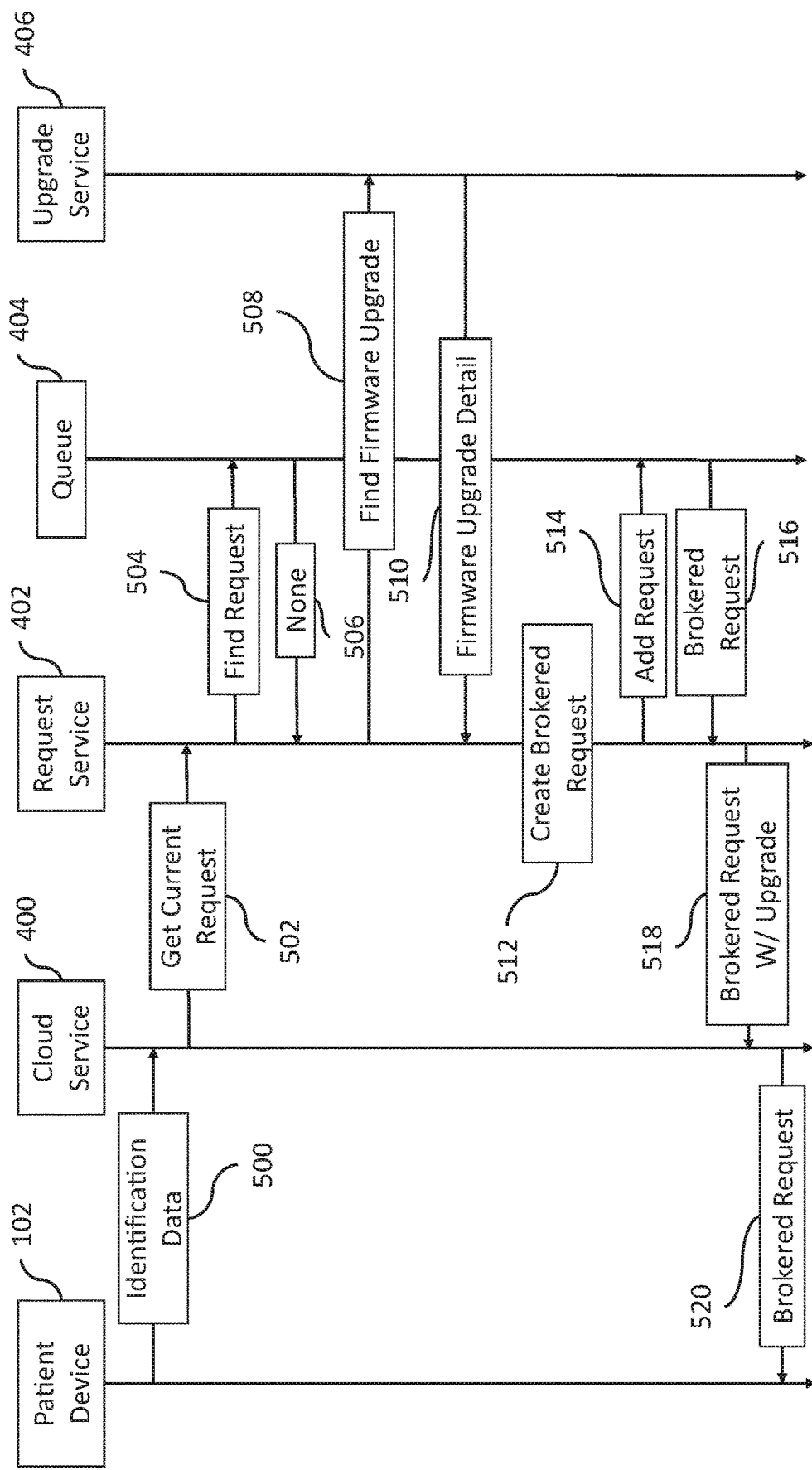
Figure 10C:
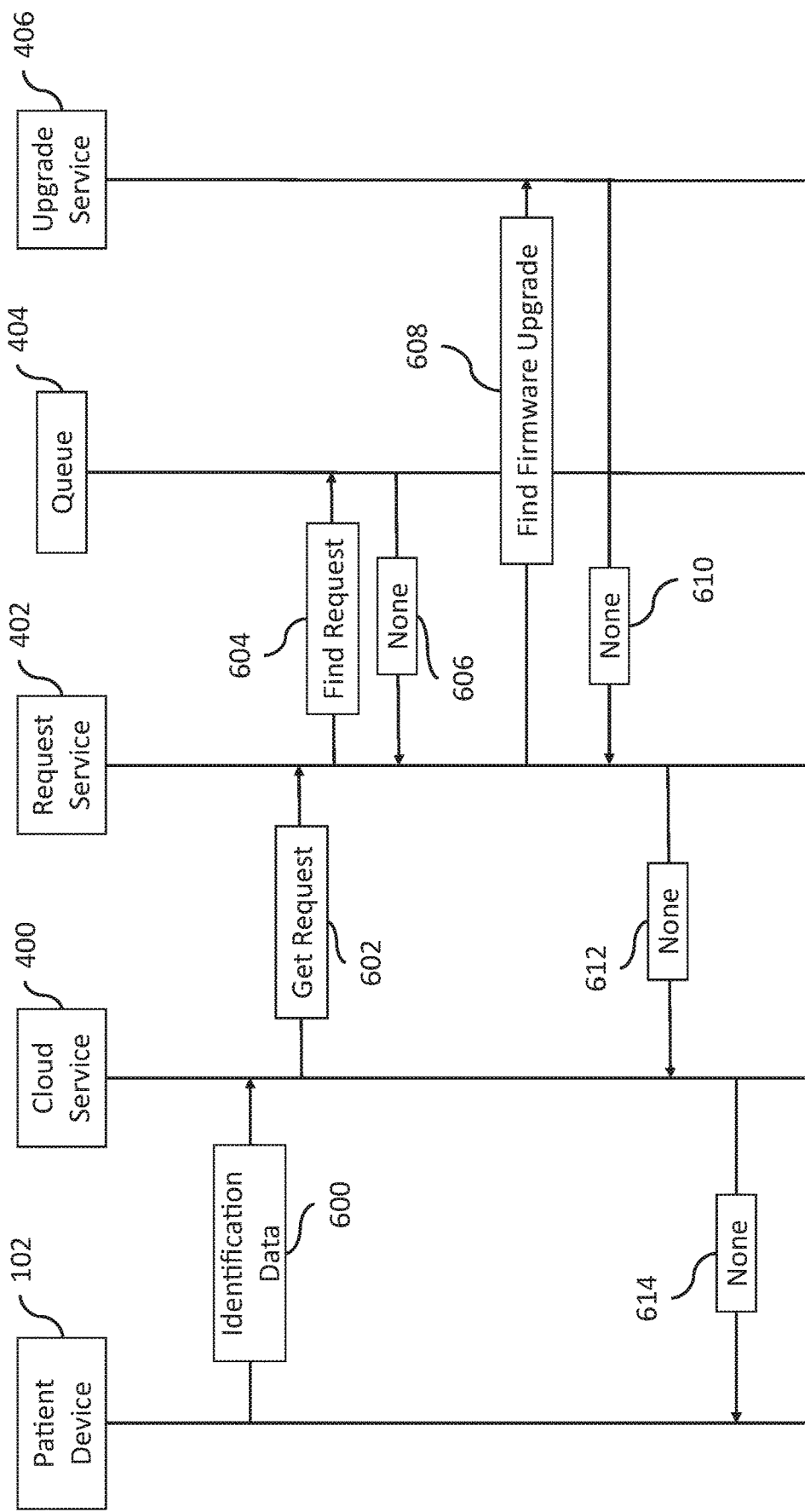

FIGS. 10A-10C show signal diagrams of communications that may occur between various computing devices and/or services in connection with delivering brokered requests to patient devices in accordance with certain examples.

4.8 Computing Device

Figure 11:
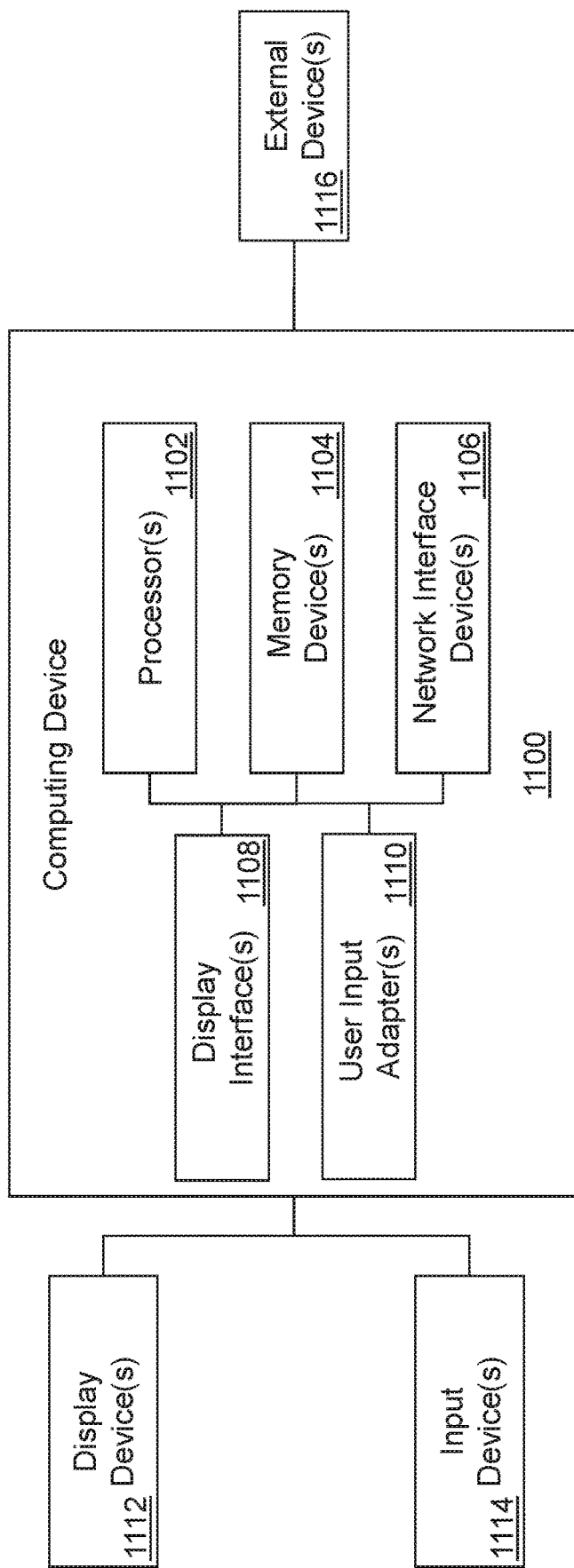

FIG. 11 shows an example computing device that may be used in some embodiments to implement features described herein.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000. In certain examples of the present technology, a supply of air at positive pressure is provided to the nasal passages of the patient via one or both nares. In certain examples of the present technology, mouth breathing is limited, restricted or prevented.

5.2 Respiratory Therapy Systems

In one form, the present technology comprises a respiratory therapy system for treating a respiratory disorder. The a respiratory therapy system may comprise an RPT device 4000 for supplying a flow of air to the patient 1000 via an air circuit 4170 and a patient interface 3000 or 3800.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.4 RPT Device

An RPT device 4000 in accordance with one aspect of the present technology comprises mechanical, pneumatic, and/or electrical components and is configured to execute one or more algorithms 4300, such as any of the methods, processes, software modules and the like, in whole or in part, that are described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

Figure 4C:
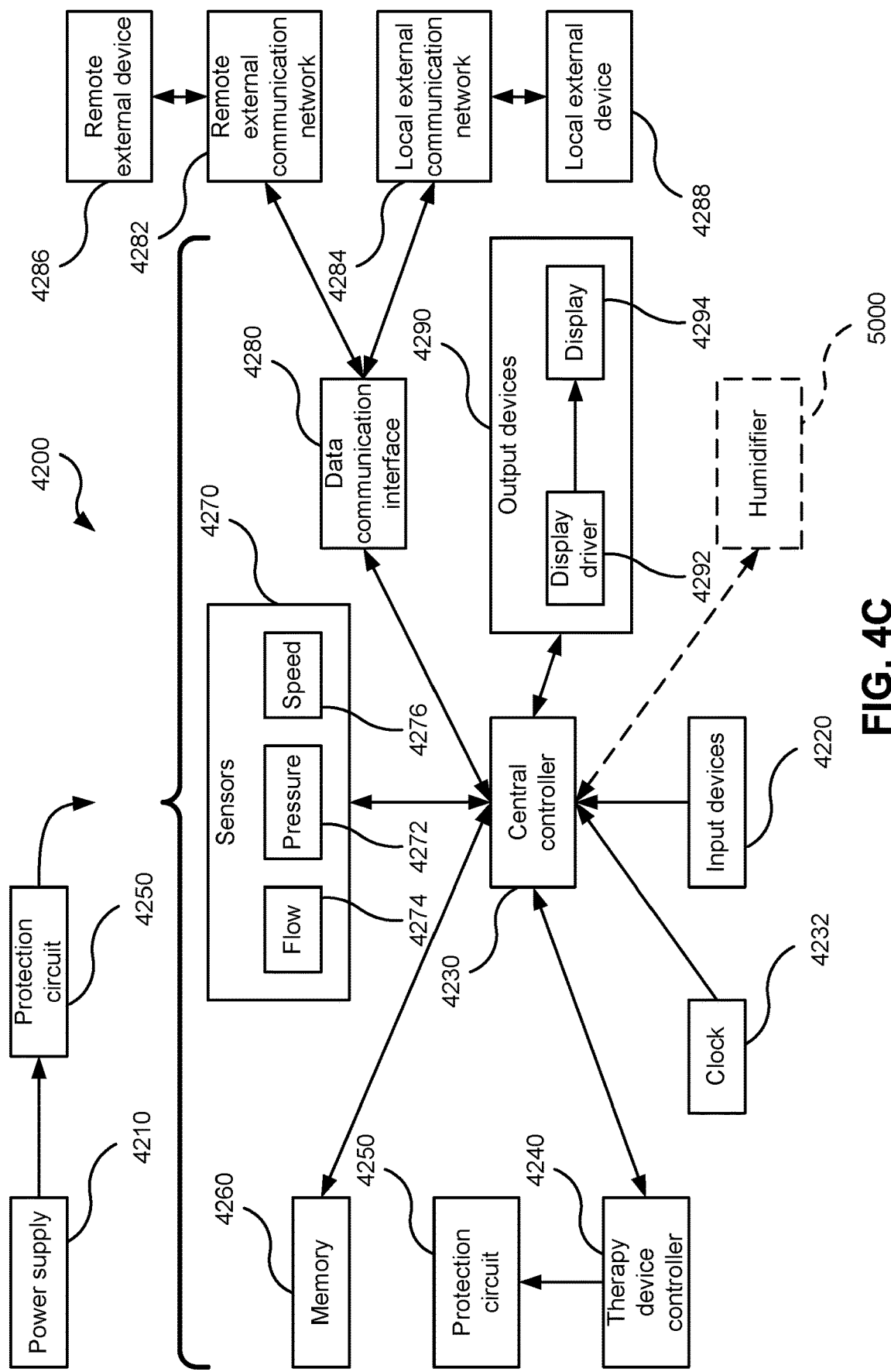
FIG. 4C is a schematic diagram of the electrical components of an RPT device in accordance with one form of the present technology.

Referring now to FIG. 4C, the RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202. In certain example embodiments, the RPT device 400 may include a computing device as is described in connection with FIG. 11. In certain examples, electrical components described in connection with FIG. 4C may correspond to their counterparts as described in FIG. 11

5.4.1 RPT Device Electrical Components
5.4.1.1 Power Supply

A power supply 4210 may be located internal or external of a housing of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.1.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.1.3 Central Controller

In one form of the present technology, the central controller 4230 is one or a plurality of hardware processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 (described in connection with FIG. 4D) expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located computing device (e.g., such as computing device 1100). For example, the remotely located device may determine control settings for a ventilator or detect respiratory related events by analysis of stored data such as from any of the sensors described herein.

5.4.1.4 Clock

The RPT device 4000 may include a clock 4232 that is connected to the central controller 4230.

5.4.1.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.1.6 Protection Circuits

The one or more protection circuits 4250 in accordance with the present technology may comprise an electrical protection circuit, a temperature and/or pressure safety circuit.

5.4.1.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.1.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control that communicates via the local external communication network 4284 with the data communications interface 4280 of the RPT device 4000.

5.4.1.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.1.9.1 Display Driver

A display driver 4292 receives as an input the characters, symbols, or images intended for display on the display 4294, and converts them to commands that cause the display 4294 to display those characters, symbols, or images.

5.4.1.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.1.10 Transducer(s)

Transducers 4270 may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of a pressure generator. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.10.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate is received by the central controller 4230.

5.4.1.10.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 is received by the central controller 4230.

5.4.1.10.3 Motor Speed Transducer

In one form of the present technology a motor speed transducer 4276 is used to determine a rotational velocity of a motor and/or a blower of the RPT device 4000. A motor speed signal from the motor speed transducer 4276 may be provided to the therapy device controller 4240. The motor speed transducer 4276 may, for example, be a speed sensor, such as a Hall effect sensor.

5.4.2 RPT Device Algorithms

Figure 4D:
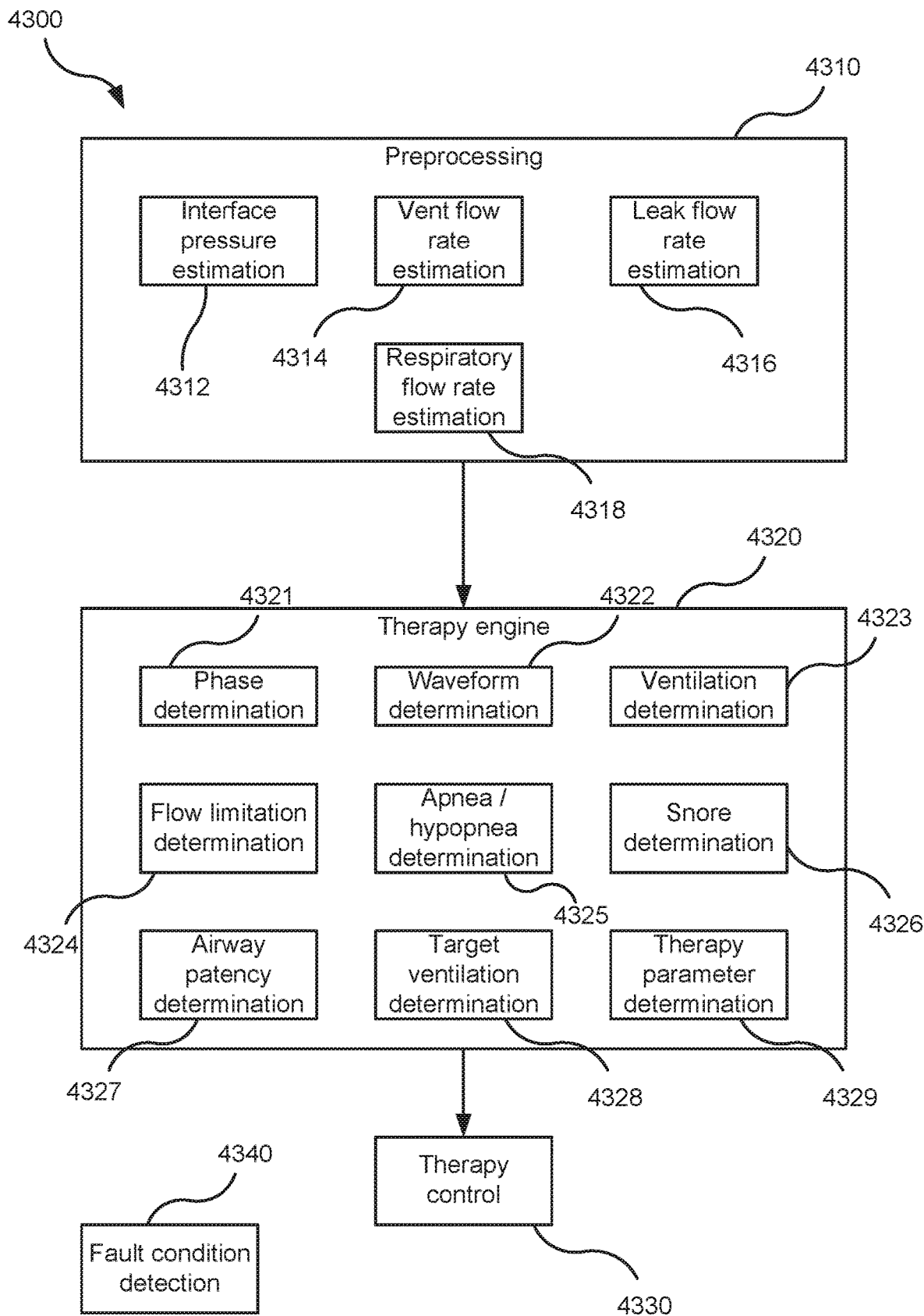
FIG. 4D is a schematic diagram of the algorithms implemented in an RPT device in accordance with one form of the present technology.

As mentioned above, in some forms of the present technology, the central controller 4230 may be configured to implement one or more algorithms 4300 as shown in FIG. 4D. These algorithms may be expressed as computer programs stored in a non-transitory computer readable storage medium, such as memory 4260. The algorithms 4300 are generally grouped into groups referred to as modules or software modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

5.4.2.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface pressure Pm, the respiratory flow rate Qr, and the leak flow rate Ql.

In various forms of the present technology, the pre-processing module 4310 comprises one or more of the following algorithms: interface pressure estimation 4312, vent flow rate estimation 4314, leak flow rate estimation 4316, and respiratory flow rate estimation 4318.

5.4.2.1.1 Interface Pressure Estimation

In one form of the present technology, an interface pressure estimation algorithm 4312 receives as inputs a signal from the pressure sensor 4272 indicative of the pressure in the pneumatic path proximal to an outlet of the pneumatic block (the device pressure Pd) and a signal from the flow rate sensor 4274 representative of the flow rate of the airflow leaving the RPT device 4000 (the device flow rate Qd). The device flow rate Qd, absent any supplementary gas, may be used as the total flow rate Qt. The interface pressure algorithm 4312 estimates the pressure drop ΔP through the air circuit 4170. The dependence of the pressure drop ΔP on the total flow rate Qt may be modelled for the particular air circuit 4170 by a pressure drop characteristic ΔP(Q). The interface pressure estimation algorithm, 4312, then provides as an output an estimated pressure, Pm, in the patient interface 3000 or 3800. The pressure, Pm, in the patient interface 3000 or 3800 may be estimated as the device pressure Pd minus the air circuit pressure drop ΔP.

5.4.2.1.2 Vent Flow Rate Estimation

In one form of the present technology, a vent flow rate estimation algorithm 4314 receives as an input an estimated pressure, Pm, in the patient interface 3000 or 3800 from the interface pressure estimation algorithm 4312 and estimates a vent flow rate of air, Qv, from a vent 3400 in a patient interface 3000 or 3800. The dependence of the vent flow rate Qv on the interface pressure Pm for the particular vent 3400 in use may be modelled by a vent characteristic Qv(Pm).

5.4.2.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000 or 3800, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.2.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.2.2 Therapy Engine Module

In one form of the present technology, a therapy engine module 4320 receives as inputs one or more of a pressure, Pm, in a patient interface 3000 or 3800, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.4.2.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase $\Phi$ of a current breathing cycle of a patient 1000.

In some forms, known as discrete phase determination, the phase output $\Phi$ is a discrete variable. One implementation of discrete phase determination provides a bi-valued phase output $\Phi$ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output $\Phi$ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase $\Phi$ equal to 0 (indicating inspiration) and 0.5 (indicating expiration) respectively.

Another implementation of discrete phase determination provides a tri-valued phase output $\Phi$ with a value of one of inhalation, mid-inspiratory pause, and exhalation.

In other forms, known as continuous phase determination, the phase output $\Phi$ is a continuous variable, for example varying from 0 to 1 revolutions, or 0 to $2\pi$ radians. RPT devices 4000 that perform continuous phase determination may trigger and cycle when the continuous phase reaches 0 and 0.5 revolutions, respectively. In one implementation of continuous phase determination, a continuous value of phase $\Phi$ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase $\Phi$ is first discretely estimated from the respiratory flow rate Qr as described above, as are the inhalation time Ti and the exhalation time Te. The continuous phase $\Phi$ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.4.2.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase $\Phi$ of a respiratory cycle of a patient according to a waveform template $\Pi(\Phi)$.

In one form of the present technology, a waveform determination algorithm 4322 provides a waveform template $\Pi(\Phi)$ with values in the range [0, 1] on the domain of phase values $\Phi$ provided by the phase determination algorithm 4321 to be used by the therapy parameter determination algorithm 4329.

In one form, suitable for either discrete or continuously-valued phase, the waveform template $\Pi(\Phi)$ is a square-wave template, having a value of 1 for values of phase up to and including 0.5 revolutions, and a value of 0 for values of phase above 0.5 revolutions. In one form, suitable for continuously-valued phase, the waveform template $\Pi(\Phi)$ comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template $\Pi(\Phi)$ is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template $\Pi(\Phi)$ from a library of waveform templates, dependent on a setting of the RPT device. Each waveform template $\Pi(\Phi)$ in the library may be provided as a lookup table of values $\Pi$ against phase values $\Phi$. In other forms, the waveform determination algorithm 4322 computes a waveform template $\Pi(\Phi)$ "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase D and time t measured since the most recent trigger instant. In one such form, the waveform determination algorithm 4322 computes the waveform template Π(Φ, t) in two portions (inspiratory and expiratory) as follows:

$$\prod(\Phi, t) = \begin{cases} \prod_i(t), \Phi = 0 \\ \prod_e(t - T_i), \Phi = 0.5 \end{cases}$$

where $\Pi_i(t)$ and $\Pi_e(t)$ are inspiratory and expiratory portions of the waveform template Π(Φ, t). In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.4.2.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

5.4.2.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow— limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.2.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.2.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.2.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.4.2.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.2.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \qquad (1)$$

where:
A is the amplitude,
$\Pi(\Phi, t)$ is the waveform template value (in the range 0 to 1) at the current value $\Phi$ of phase and t of time, and
$P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.4.2.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose interface pressure Pm at the patient interface 3000 or 3800 is equal to the treatment pressure Pt.

5.4.2.4 Detection of Fault Conditions

In one form of the present technology, the central controller 4230 executes one or more methods 4340 for the detection of fault conditions. The fault conditions detected by the one or more methods 4340 may include at least one of the following:

Power failure (no power, or insufficient power)
Transducer fault detection
Failure to detect the presence of a component
Operating parameters outside recommended ranges (e.g. pressure, flow rate, temperature, $PaO_2$)
Failure of a test alarm to generate a detectable alarm signal.

Upon detection of the fault condition, the corresponding algorithm 4340 signals the presence of the fault by one or more of the following:

Initiation of an audible, visual &/or kinetic (e.g. vibrating) alarm
Sending a message to an external device
Logging of the incident

5.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

In particular, the air circuit 4170 may be in fluid connection with the outlet of a pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230.

5.6 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

The humidifier reservoir 5110 may comprise a water level indicator 5150 as shown in FIG. 5A-5B. In some arrangements, the humidifier reservoir dock 5130 may comprise a locking feature such as a locking lever 5135 configured to retain the reservoir 5110 in the humidifier reservoir dock 5130. According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable.

5.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak−0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Respiratory Therapy Modes

Various respiratory therapy modes may be implemented by the disclosed respiratory therapy system.

5.8.1 CPAP Therapy

In some implementations of respiratory pressure therapy, the central controller 4230 sets the treatment pressure Pt according to the treatment pressure equation (1) as part of the therapy parameter determination algorithm 4329. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for the therapy engine module 4320 to determine phase Φ or the waveform template Π(Φ).

In CPAP therapy, the base pressure $P_0$ may be a constant value that is hard-coded or manually entered to the RPT device 4000. Alternatively, the central controller 4230 may repeatedly compute the base pressure $P_0$ as a function of indices or measures of sleep disordered breathing returned by the respective algorithms in the therapy engine module 4320, such as one or more of flow limitation, apnea, hypopnea, patency, and snore. This alternative is sometimes referred to as APAP therapy.

Figure 4E:
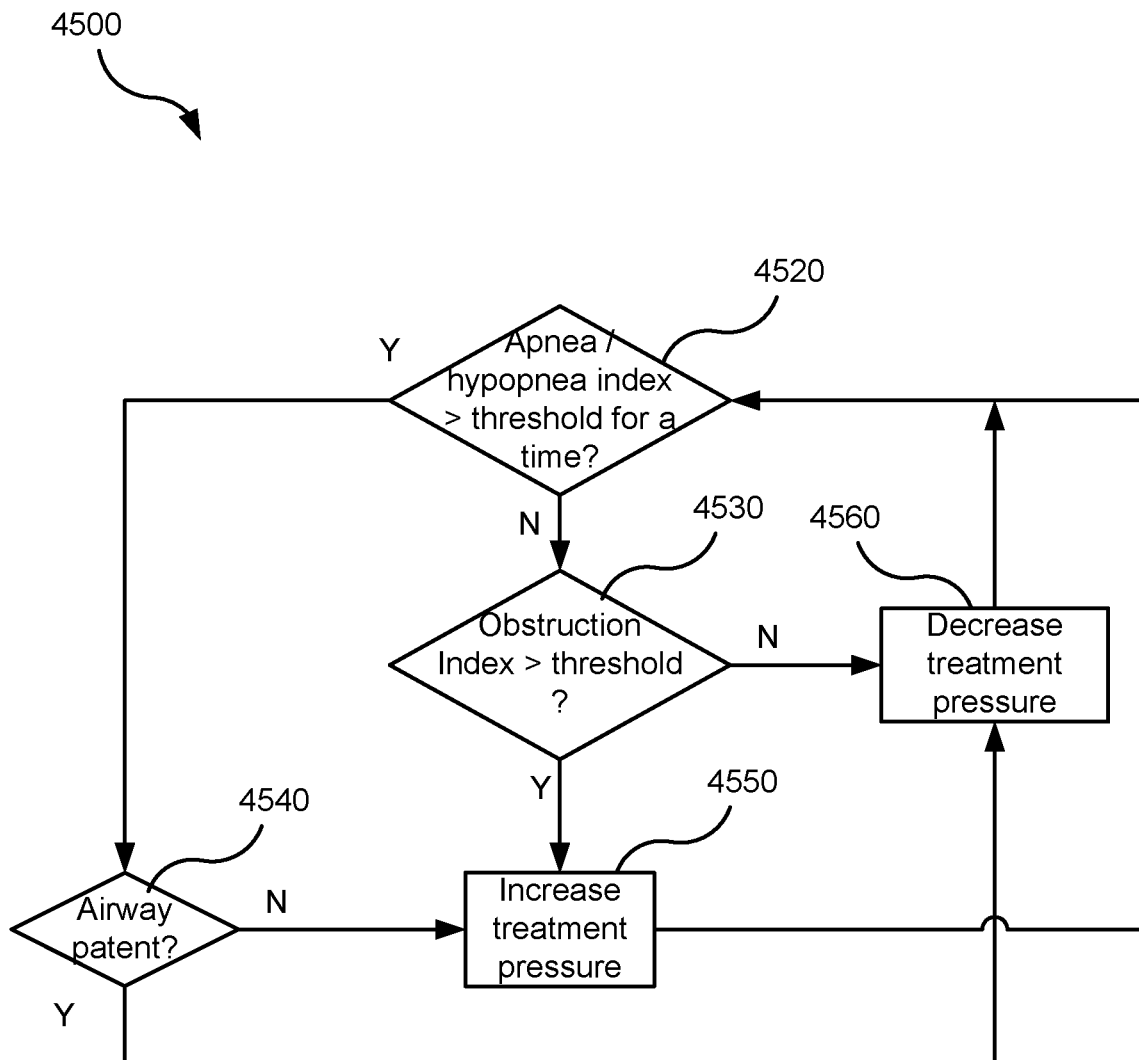
FIG. 4E is a flow chart illustrating a method carried out by the therapy engine module of FIG. 4D in accordance with one form of the present technology.

FIG. 4E is a flow chart illustrating a method 4500 carried out by the central controller 4230 to continuously compute the base pressure $P_0$ as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment $\Delta P$, provided the resulting treatment pressure Pt would not exceed a maximum treatment pressure Pmax. In one implementation, the predetermined pressure increment $\Delta P$ and maximum treatment pressure Pmax are 1 cmH$_2$O and 25 cmH$_2$O respectively. In other implementations, the pressure increment $\Delta P$ can be as low as 0.1 cmH$_2$O and as high as 3 cmH$_2$O, or as low as 0.5 cmH$_2$O and as high as 2 cmH$_2$O. In other implementations, the maximum treatment pressure Pmax can be as low as 15 cmH$_2$O and as high as 35 cmH$_2$O, or as low as 20 cmH$_2$O and as high as 30 cmH$_2$O. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$-Pmin, so that the decrease in $P_0$ to the minimum treatment pressure Pmin in the absence of any detected events is exponential. In one implementation, the constant of proportionality is set such that the time constant r of the exponential decrease of $P_0$ is 60 minutes, and the minimum treatment pressure Pmin is 4 cmH$_2$O. In other implementations, the time constant r could be as low as 1 minute and as high as 300 minutes, or as low as 5 minutes and as high as 180 minutes. In other implementations, the minimum treatment pressure Pmin can be as low as 0 cmH$_2$O and as high as 8 cmH$_2$O, or as low as 2 cmH$_2$O and as high as 6 cmH$_2$O. Alternatively, the decrement in $P_0$ could be predetermined, so the decrease in $P_0$ to the minimum treatment pressure Pmin in the absence of any detected events is linear.

5.8.2 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000. That is, based on the typical waveform templates $\Pi(\Phi, t)$ described above, the therapy parameter determination algorithm 4329 increases the treatment pressure Pt to $P_0+A$ (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few cmH$_2$O) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 cmH$_2$O. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm 4329 takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation (1) to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm 4328 from the typical recent ventilation Vtyp, as described above.

In some forms of servo-ventilation, the therapy parameter determination algorithm 4329 applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A = G \int (\text{Vent} - \text{Vtgt}) dt \qquad (2)$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 cmH$_2$O/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The value of the pressure support A computed via equation (2) may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure $P_0$. As with the base pressure $P_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure $P_0$ in constant CPAP therapy.

Alternatively, the therapy parameter determination algorithm 4329 may repeatedly compute the base pressure $P_0$ during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

5.9 Data Management System

FIG. 7 shows an example Machine Management Services System 106 that is used to communicate with, and provide updates to, patient devices 102 (102A, 102B, 102C) in accordance with certain examples. FIG. 8 shows a signal diagram that shows communications between an example patient device and the example Machine Management Services System of FIG. 7. It will be appreciated that the examples provided in at least FIGS. 7-10C should not be considered as limiting the scope of the disclosure or usefulness of the features described herein.

Turning to FIG. 7, patient devices 102 communicate with machine management services (MMS) system 106 via network 104. MMS system 106 may include one or more computing devices (e.g., as described in connection with FIG. 11). In certain examples, certain functionality provided by the MMS system 106 may be provided on cloud-based computing architecture (e.g., via Amazon AWS, Microsoft Azure, etc.).

It will also be appreciated that while three different Patient devices 102 (102A, 102B, and 102C) are shown in FIG. 7 communicating with MMS system 106, that any number of patient devices may be provided and be in communication with MMS system. In other words, MMS system 106 may be configured to communicate with one or more fleets (each of which includes multiple individual patient devices) of patient devices that are used by patients across the world.

Patient devices may include different types of patient devices. For example, a patient device may be RPT 4000, humidifier 5000, or patient interface 3000. In certain examples, patient devices may include components that are part of an individual patient device. For example, a patient device that is an RPT device may include a cellular modem that is used to communicate, via network 104, with MMS system 106. Components of patient devices may include different hardware and/or software components of the device. For example, a Bluetooth software driver may be one component and another component may be an application that controls how a flow generator works for AutoSet. Another component may be the BIOS for a SoC that is used to control a flow generator. In certain examples, any type of device or component that operates software, firmware, or is otherwise programmable may be considered a patient device according to the techniques described herein. In other words, components of patient devices may themselves be considered "patient devices" according to the techniques discussed herein.

In general, individual patient devices 102 may include any of the components that are described in connection with FIG. 11 and/or FIG. 4C. For example, a flow generator may include one or more processors 1102; one or more memory devices 1104; and one or more network interface devices 1106. One of the network interface devices may be, for example, a Bluetooth transceiver. In certain examples, a given patient device may communicate with another computing device (e.g. a mobile phone or a personal computer), which may then relay the communications or messages provided from the patient device to MMS system 106. Components may also be associated with or have firmware, software, or the like that allow for using a given component.

In many places in this document, including but not limited to in the description of FIG. 7, software modules (and the like) and actions performed by software modules (and the like) are described. This is done for ease of description and it should be understood that, whenever it is described in this document that a software module perform any action, the action is in actuality performed by underlying hardware elements (such as a processor and a memory device) according to the instructions that comprise the software module. Further details regarding this are provided below in, among other places, the description of FIG. 11.

As discussed herein, patient devices 102 may communicate one or more pieces of identification data. This is shown at 200 in FIG. 8. Identification data may include, for example a version number, a region identifier or name, a component type (e.g., the component for which the version applies to), or other identifier. In certain examples, the identification data that is transmitted from the patient device may be data that is agnostic to the patient(s) using the patient device. In other words, the identification data that is transmitted may exclude patient identifying data. This type of implementation may be advantageous in certain examples as patient data does not need to be acquired or transmitted to the MMS system 106 in order for upgrade packages to be deployed to individual patient devices.

In certain examples, the identification data that may be transmitted includes unique identifiers that are associated with a transceiver included with the patient device 102. For example, a cellular identifier that is associated with a cellular transceiver/module included with the patient device 102. In certain examples, the identifier may uniquely identify a given patient device 102. In certain other examples, the identification data may include an identifier for a patient. In certain examples, the device identification data that is transmitted from each patient device 102 is unique (e.g., a GUID/UUID or the like) such that it can be used to determine (by the MMS 106) what other components or devices are included with the patient device (e.g., by consulting status DB 112).

In any event, MMS system 106 receives messages from and delivers messages to each patient device 102. MMS system 106 may include a rule manager module 108 that is configured to determine, based on information transmitted from a corresponding patient device, if an upgrade package should be delivered to the corresponding patient device (or associated computing device). As explained in greater detail below, in certain examples, the determination of whether an upgrade package should be delivered may be additionally based on data that is stored in the status DB 112.

MMS system 106 may include a rules database 110 that stores the rules used by the rule manager module 108, status database 112, pending requests database 114, and upgrade packages 116. As used herein, the term database includes any organized collection of data on a computer system and may include, for example a relational database, an XML or JSON (or other file type) file, etc.

In certain example embodiments, the MMS system 106 allows for upgrade requests to be processed in a stateless manner such that the MMS system 106 does not need to track whether individual upgrade requests (e.g., jobs) are processed correctly by each individual patient device 102. This type of implementation can provide benefits over other types of stateful implementations (e.g., job based systems).

Rule manager module 108 performs processing for determining what upgrade package should be applied and/or delivered to a given patient device 102. This process is described in greater detail in connection with FIGS. 8 and 9B, but may include, for example, using device identification data (e.g., transmitted from patient device 102B at 200) to determine the various components of that device (e.g., those that have updatable data fields, software, and/or firmware), determine which components have possible updates that can be applied, and then delivering those updates (or notifying of the existence of such updates) to the patient device for updating and/or installation thereon. Such a process may include obtaining device profile information from status database 112 at 201 and checking that data against one or more rules at 202 to determine (at 204) which upgrade package should be delivered to a patient device 102 at 206.

Each rule may be a separate entry or record in the rules database 110 and each rule may correspond to an upgrade package that includes one or more upgrades for firmware/software/settings or all of the above. Each rule may indicate or define a version or other data for a component of the patient device that is used to trigger a given rule. Each rule may also indicate a task or upgrade file that is be applied or communicated to the patient device when the corresponding rule is triggered. Examples of rules that may be stored in rules database 110 are shown in connection with Tables 1-4 below.

It will be appreciated that the term "upgrade" as used herein is intended to cover situations in which changes occur to data, software, or firmware of a device. Thus, in some instances, an "upgrade" may include a downgrade where, for example, a previously applied update is being rolled back (e.g., due to a security flaw, etc.). For example, an "upgrade" package may be delivered that changes re-installs or rolls back from version 10 of an application to version 9.

MMS system 106 also may include a status database 112 that includes records of the currently installed versions/settings for components of each patient device. Example data that may be included in the status database 112 may be similar to the "IdentificationProfiles" that are shown in Tables 2-4 and 8 below, with the various components of a given device each being stored in connection with a version or other identifier that is used to identify the firmware or software (or setting) version that is currently in use by the component of the device. In certain examples, the rules manager module 108 may use the status database 112 to acquire versioning information for each component of a given device that is specified by the provided identification data. For example, the identification data that is communicated to the MMS system from a given device may be a GUID or other unique identifier that is then used to lookup all of the components (and associated versioning information) included with the given device. Such information may then be used to determine whether any of the rules 110 are applicable (via the rule manager module 108) for components that are installed on the given patient device. Status database 112 may be a data store for all of the characteristics, properties, or other configuration information for a given device. Storing such information within the MMS system 106 can advantageously allow the information to be retrieved without having the patient device transmit such information each time the patient device checks in with the MMS system 106 to determine if an upgrade is available.

However, in certain examples, some or all of the data that is stored in the status database 112 can be communicated (e.g., each time) when an individual patient device checks in with the MMS system 106.

In certain example embodiments, the status database 112 is populated with component information when each individual patient device is manufactured. At the time of manufacturing the device (or a component thereof) may be assigned a unique identifier. At this time the unique identifier may be stored in association with the component data for the various components that are included with the device. In certain examples, a vendor or other third-party may also provide data regarding versioning and component information for individual devices. In certain examples, the status database 112 may include organization and/or region identifiers that are also stored in association with each unique patient device identifier. Such information may be used to advantageously target upgrade packages to particular organizations and/or particular regions in the world (e.g., upgrade packages that are for patient devices in China).

Pending requests 114 may include a list/queue (or other data structure) of all currently pending requests. In certain examples, pending requests are a collection of requests (e.g., that a device take some particular action, including applying firmware or software upgrades or changes to settings) that are pending and yet to be communicated to individual patient devices. In certain examples, as discussed herein, when a patient device checks-in and supplies device identification data, that data may be used to lookup if there are any pending requests for that device.

The MMS system 106 communicates with a given patient device and instructs it to handle specific requests. Requests may be to apply a specific upgrade package (e.g., to download a file and install it). In certain examples, once a request has been communicated to a patient device and has been added to the pending requests 114, MMS system 106 will not track the successful completion of that specific request. This may provide for the above mentioned stateless system for how requests are handled by the MMS system 106. In certain other examples, a record of the pending request that is communicated to the patient device is maintained within the pending requests 114 and marked as "in progress" or "successfully completed" or the like, based on notifications or other information provided by the patient device. This latter implementation may provide for a stateful system in how requests are handled by MMS system 106 (e.g., by tracking the state of the requests). In certain examples (and applicable to both of the above implementations), MMS system 106 may track some informational status and/or failure condition(s) as reported by the patient device and store such information in pending requests 114. Pending requests 114 may be stored in a queue or other data structure (e.g., as queue 404 in FIGS. 10A-10C). In certain examples, pending requests 114 may be stored in a database or the like.

Upgrade packages 116 may be a data store for all upgrade packages that may be applied to any of the patient devices. Upgrade packages can include code changes to software or firmware and/or setting changes for adjusting one or more parameters of a given patient device. Such parameter, software, and/or firmware changes may then affect or change how the patient device operates. For example, the fan or blower operation of a flow generator of an RPT device may be adjusted to more effectively provide treatment to a patient. As discussed elsewhere herein, in certain examples, adjustment of settings of a patient device may require additional authorization from a clinician or other medical professional. Thus, in certain examples, the rule manager module may rely on such additional input to determine whether an upgrade (e.g., a setting change) should be applied. In certain examples, the upgrade packages may include any or all of the following: security enhancements, additional features (e.g., such as a new mode of therapy that is now available on the RPT device), different languages (e.g. a different language pack that includes either different audio and/or text—to update language strings embedded in the RPT device), a patient survey or questionnaire, patient coaching or tips, or other settings, configuration, or applications.

In certain example embodiments, upgrade packages 116 stores a list of network or website addresses of where each upgrade file/data may be acquired by patient devices. Thus, the MMS system 106 may be configured to provide the links to where the upgrade files may be found instead of the upgrade files themselves. In certain examples, the actual installation files may be stored separately from the MMS system 106.

Tables 1-4 below provide an example of an upgrade specification that may be found in connection with Rules database 110. Table 1 shows how an upgrade specification may be structured in connection with multiple different rules that use identification profiles to trigger a corresponding upgrade package. Each rule includes an identification profile that may be a subset of the device profile data that is stored for each patient device in status database 112. Different rules (also called segments of an upgrade specification) and the identification profiles used to trigger those rules, along with the upgrade package to be provided in connection with each identification profile, are shown in connection with tables 2, 3, and 4. Each trigger (e.g., the precondition) may be associated with a unique identifier to allow the MMS system 106 to refer and/or track that rule (segment). This may allow for determining how many times a given upgrade has been provided across a fleet of devices.

TABLE 1

| Upgrade Example Specification |
|---|
| {<br>"UpgradeSpec": [<br>{<br>//Example A - Shown in Table 2<br>},<br>{<br>//Example B - Shown in Table 3<br>},<br>{<br>//Example C - Shown in Table 4<br>},<br>]<br>} |

In Table 2, an upgrade from version 4.0.1 to 4.0.3 of the FG AutoSetApplication is triggered when device identification data for the flow generator component includes the following version values: 1) "'BootloaderIdentifier': 'SW03901.00.3.0.0.48255'"; 2) "'ApplicationIdentifier': 'SW03900.01.4.0.1.50578', and 3) "'ConfigurationIdentifier': 'CF03900.01.03.00.50578'. If this precondition is met, then the rule manager module 108 determines that the indicated "UpgradeFile" should be applied to the component of the patient device in question. The patient device is notified and the indicated upgrade file is applied by the patient device. In certain examples, once the "PostCondition" values are met, then the status DB 112 may be updated to reflect that the corresponding device has been updated (e.g., to 4.0.3). In certain examples, the post condition part of the rule may be ignored.

TABLE 2

| Upgrade Example A |
|---|
| {<br>"Comment": "FG AutoSetApplication 4.0.1 to 4.0.3",<br>"UpgradeFile": "CS03900.01.4.0.3.03.00.50927_NoRegion_AutoSet.ota",<br>"UpgradeFileHash":<br>"0e7343cfe0da88e913a7302fc17bc2e4df83297902b5dec4b01bda83375daa64",<br>"PreCondition": {<br>"FlowGenerator": {<br>"IdentificationProfiles": {<br>"Software": {<br>"BootloaderIdentifier": "SW03901.00.3.0.0.48255",<br>"ApplicationIdentifier": "SW03900.01.4.0.1.50578",<br>"ConfigurationIdentifier": "CF03900.01.03.00.50578"<br>}}}}<br>,<br>"PostCondition": {<br>"FlowGenerator": {<br>"IdentificationProfiles": {<br>"Software": { |

TABLE 2-continued

Upgrade Example A

"ApplicationIdentifier": "SW03900.01.4.0.3.50927",
"ConfigurationIdentifier": "CF03900.01.03.00.50927"
}}}}

In Table 3, an upgrade from version 4.0.2 to 4.0.3 of the FG AutoSetApplication is triggered when device identification data the flow generator component includes the following values: 1) "'BootloaderIdentifier': 'SW03901.00.3.0.0.48255"; 2) "'ApplicationIdentifier': 'SW03900.01.4.0.2.50813, and 3) "'ConfigurationIdentifier': 'CF03900.01.03.00.50813'. If this precondition is met, then the rule manager module 108 determines that the indicated "UpgradeFile" should be applied to the component of the patient device in question. The patient device is notified and the indicated upgrade file is applied. In certain examples, once the "PostCondition" values are meet, then the status DB 112 may be updated to reflect that the corresponding device has been updated (e.g., to 4.0.3). It will be appreciated that Tables 2 and 3 show upgrade packages to the same version for the same component. However, because the preconditions are different, two different identification profiles may be used in order to trigger upgrades for patient devices that have differently versioned components.

TABLE 3

Upgrade Example B

"Comment": "FG AutoSetApplication 4.0.2 to 4.0.3",
"UpgradeFile": "CS03900.01.4.0.3.03.00.50927_NoRegion_AutoSet.ota",
"UpgradeFileHash":
"0e7343cfe0da88e913a7302fc17bc2e4df83297902b5dec4b01bda83375daa64",
"PreCondition": {
"FlowGenerator": {
"IdentificationProfiles": {
"Software": {
"BootloaderIdentifier": "SW03901.00.3.0.0.48255",
"ApplicationIdentifier": "SW03900.01.4.0.2.50813",
"ConfigurationIdentifier": "CF03900.01.03.00.50813"
}}}}
,
"PostCondition": {
"FlowGenerator": {
"IdentificationProfiles": {
"Software": {
"ApplicationIdentifier": "SW03900.01.4.0.3.50927",
"ConfigurationIdentifier": "CF03900.01.03.00.50927"
}}}}

In Table 4, a Bluetooth iOS Upgrade is triggered when device identification data the flow generator component includes the following values: 1) "'ApplicationIdentifier': 'SW03900.01.4.0.3.50927'" and the device identification data for the Bluetooth Module component includes the following values: 1) "'ApplicationIdentifier': 'ST266.1.1.2.182.2'". Accordingly, a precondition may include versioning data for multiple components of a system. If this precondition is met, then the rule manager module 108 determines that the indicated "UpgradeFile" should be applied to the component of the patient device in question. The patient device is notified and the indicated upgrade file is applied. In certain examples, once the "PostCondition" values are meet, then the status DB 112 may be updated to reflect that the corresponding device has been updated (e.g., to ST266.1.1.3.199.2).

TABLE 4

Upgrade Example C

"Comment": "Bluetooth iOS Upgrade",
"UpgradeFile": "ST266.1.1.3.199.2.ota",
"UpgradeFileHash":
"ebad06fc34d6214679a982593eb6d23d58da31a760e41495e18efb2eb3be4cf7",
"PreCondition": {
"FlowGenerator": {

TABLE 4-continued

Upgrade Example C

```
"IdentificationProfiles": {
"Software": {
"ApplicationIdentifier": "SW03900.01.4.0.3.50927"
}
}
},
"BluetoothModule": {
"IdentificationProfiles": {
"Software": {
"ApplicationIdentifier": "ST266.1.1.2.182.2"
}}}}
,
"PostCondition": {
"BluetoothModule": {
"IdentificationProfiles": {
"Software": {
"ApplicationIdentifier": "ST266.1.1.3.199.2"
}}}}
```

Once the proper rule and corresponding upgrade package for that rule has been identified based on the provided device identification data (and/or the retrieved device profile data from the status DB 112), then the patient device 102 may be notified of the upgrade package at 206. In certain examples, this may include providing the data that is to be applied for the upgrade within the message that is delivered from the MMS system 106. In other examples, the delivery of the upgrade package may include specification of a URI or other address (along with other data, such as has information, size, file name, and the like) to allow for future downloading of one or more files by using the indicated URI.

At 208, the patient device applies the upgrade package. This may include validating that the upgrade package is complete, correct, or otherwise not corrupted (e.g., performing checksum, etc.) and then writing over existing settings and/or installing software and/or firmware updates.

Once an upgrade is installed by a patient device, then the patient device 102 may check back in with the MMS system 106 and communicate the new version information of the updated component to the MMS system 106. The updated version information may then be stored within the status DB 112 (e.g., by overwriting the prior value) in connection with that patient device and the given component. Accordingly, the MMS system 106 is kept up-to-date on the firmware/software/setting versions that are currently installed on a given patient device. This type of implementation also can advantageously allow for the system to be implemented without having continually track individual upgrade requests. In certain examples, upon completion of the upgrade by the patient device 102, the patient device 102 may communicate back to the MMS system 106 a status update. This message may include device identification data and/or component identification data (e.g., software or firmware versions) that is then used to, by the MMS system 106, verify that the update has been performed/installed by the patient device 102. In certain examples, the patient device 102 may communicate back to the MMS system 106 its progress in the upgrade process or whether a failure has occurred that prevents the patient device 102 from successfully completing the request. This progress or failure information may be stored by the MMS system 106 in the pending requests 114. Progress information may include, for example, that a file has been successfully downloaded, that the upgrade is being applied, that it is in progress, that it is completed and the patient device is rebooting, etc.

It will be appreciated that the ability to create individual rules that may be included into the overall rule specification allows for an automated system for managing updates that can scale across thousands or millions of different patient devices. This is realized because communication from the individual patient devices prompts the rule manager module 108 to appropriately select, based on device profile data acquired from status DB 112 and the rule specification from rules 110, the correct upgrade packages to send to the individual patient devices. There may thus not be as much of a need to manually monitor the upgrading of patient devices when new upgrade packages are made available that can be installed/applied to those devices.

FIGS. 9A and 9B are flow charts of computer operations that may be executed in certain examples, such as by, respectively, patient device 102 and MMS system 106. FIG. 9A shows example client-side processing that may be performed on an example patient device 102 and FIG. 9B shows example server-side processing that may be performed by one or more processors of MMS system 106.

In FIG. 9A, at 300, the patient device determines whether or not it should perform a check-in process. This check may be performed every day, week, month, etc. In certain examples, clock 4232 may be used to determine when the check-in process should be performed. If it is not time for a check-in, then the process returns to 300.

At 302, if the check in process is to be performed, then the patient device 102 transmits device identification data to another computer system, such as MMS system 106. As discussed herein, device identification data may be a GUID for or associated with the patient device (e.g., such that it is unique amongst every other patient device). In certain example embodiments, the GUID is assigned to the network interface that is used by the patient device 102. In certain alternative examples, the transmitted data may include transmission of software/firmware/setting version information. It will be appreciated that while the term GUID is used in connection with certain examples herein that other identifiers (whether unique or not) may also be used to facilitate identification of a patient device or a component thereof.

At 304, after transmission of the device identification data, the patient device 102 receives an upgrade data package from MMS system 106. In certain example embodiments the upgrade data package may include a link, URI, or other location at which the file(s) for the upgrade may be downloaded. Thus, upon receiving such information within the upgrade data package at 304, the patient device may then submit a request to the indicated location (e.g., a remote computer system) and retrieve the files specified by the upgrade data package. Upon reception of such files, the process may then proceed to step 306.

In certain example embodiments, the upgrade data package may include (or be) data for settings or other parameters that are to be modified on the patient device. Table 5 shows an example of a "BrokerItem" element that may be included as part of an upgrade data package that is delivered to a patient device via step 304.

TABLE 5

"BrokerItem" : {
"ResponseCallbackUri": "/v1/cloud/requests/item/ {uuid-ri-1}/status",
"RequestType" : "ConfigurationProfiles",
"RequestContent": {
"ConfigurationProfiles": {
"DataDeliveryControl " : {
},
"SettingProfilesCollection": { "Delivery": "On" },
"TherapyOneMinutePeriodic": { "Delivery" : "Off" } ,
"ClimateOneMinutePeriodic": { "Delivery" : "Off" } ,
"DiagnosticOneMinutePeriodic": { "Delivery" : "Off" } ,
"MachineMetrics": { "Delivery" : "On" } ,
"UsageEvents": { "Delivery": "On" },
"TherapyEvents": { "Delivery" : "On" },
"SystemExceptionEvents" : { "Delivery": "On" } ,
"SystemActivityEvents": { "Delivery": "On"},
"DiagnosticExceptionEvents": { "Delivery": "Off" },
"Summary" : { "Delivery" : "On" }
"DataOnOemandControl ": {
"SettingProfilesCollection": {
"FromDateTime": "2018-02-07T00:00:00Z",
"ToDateTime" : "2020-02-97T11:59:59Z"
),
"TherapyOneMinutePeriodic": { . ... },
"ClimateOneMinutePeriodic": { } ,
"DiagnosticOneMinutePeriodic": . ... } ,
"MachineMetrics": { . ... },
"UsageEvents": { },
"TherapyEvents " : { . . . },
"SystemExceptionEvents" : { },
"SystemActivityEvents": { ... },
"DiagnosticExceptionEvents": { ... },
"Summary" : { }

Accordingly, once the patient device 102 receives this BrokerItem that is included in the upgrade data package, it may be applied to the configuration profiles for the patient device.

In certain example embodiments, the contents of the upgrade data package may also include the software or firmware that is to be applied to the patient device 102. Thus, instead of separately requesting the software or firmware files (e.g., as is shown in Table 9) after receiving the upgrade data package from MMS system 106, such files may be provided in conjunction with the upgrade data package.

At 306, the received upgrade data package is validated by the patient device. This may include validating the message sent by the MMS system 106 and/or validating the upgrade file that is separately retrieved. This may include hashing the received data or other file and comparing the hash to a hash value that was included in the upgrade data package message. In certain examples, the validation may include comparing the file size that is expected to be received (e.g., that is indicated by MMS system 106) to the actual file size of the file that has been retrieved. If the validation of the upgrade file fails, then the patient device may retry to download the file. In certain examples, the patient device may notify the MMS system of failure of the download or of the message or file validation. The failure may be logged by the MMS system 106 (or other device) for future analysis and/or reporting.

In certain examples, a download failure of an upgrade file may terminate the client side processing (e.g., after reporting the failure to MMS system 106) and the process may return to 300 and wait until the next check-in time is activated. Upon checking in again, the patient device may then be provided with the same upgrade data package for which the upgrade previously failed.

At 308, once the validation is successful, then the upgrade data package may be applied to the patient device 102. This may include, for example, overwriting or replacing certain parameter values that are used by the patient device 102 and/or installing or otherwise applying software and/or firmware updates to the patient device. The installation procedure may also be validated by the patient device (e.g., if the installation failed or was successful).

At 310, the patient device transmits the status of the upgrade back to the MMS system 106. In certain example embodiments, this may include reporting the current versioning information of the component that was just upgraded on the patient device. In certain examples, the status report may be for multiple different components (e.g., a flow generator and Bluetooth module). In certain examples, the status report may be related to the upgrade request as a whole (e.g., that it was successful). Table 6 shows an example element that may be transmitted to the MMS System 106. In certain example embodiments, the contents of Table 6 may be transmitted from the patient device to the MMS system 106 upon reception of the upgrade data package at 304 (e.g., to validate the request is received, or any failures that occurred in connection with the request)

TABLE 6

"BrokerItemStatus": {
"RequestType" : "ConfigurationProfiles",
"RequestStatus": "( RequestReceivedSuccess
| RequestParseFailure
| CellularModuleIdentifierMatchFailure
| FlowGeneratorIdentifierMatchFailure
| OxygenConcentratorIdentifierMatchFailure
| RequestTypeFailure
| RequestContentFailure)"
}

In certain examples, a device status that is transmitted at 310 may include either a notification of failure to apply an upgrade (and possibly a failure error code or message) or the versioning information of the component(s) that was just upgraded. In other words, in certain examples the success of an upgrade will be implicitly provided by the patient device providing the current versioning information to the MMS system 106. Accordingly, the MMS system may be informed as to the status of the patient device 102 and/or the upgrade package that was supplied to the patient device.

FIG. 9B shows example server-side processing that may be performed by the MMS system 106.

At 350, device identification data is received from a patient device. As discussed herein, the device identification data may be provided in various different ways. Table 7 below provides an example of how device identification data may be submitted to the MMS system 106.

TABLE 7

GET /v1/cloud/requests/item/flowgenerators/paired/cellularmodules/{uid} HTTP/1.1
Authorization:
Content cellularModule=" {cm-uid}" content=" {content}",
Encryption cellularModule="{cm- uid}" initializationVector=" {vector}",
Signature cellularModule=" {cm-uid }" signature=" {signature}"

In the above example from Table 7, the GUID (the uid in the URI) that uniquely identifies the requesting patient device is the cellular ID that is paired with the patient device (in this case a flow generator). This ID is unique as it is assigned to every cellular module that is manufactured and thus may be used to uniquely identify the patient device that is paired with that cellular module. This is submitted as part of an HTTP get method to the MMS system 106.

At 351, the MMS system 106 uses the provided device identification data used to lookup the device profile data (e.g., all of the components) of the indicated patient device by referencing status database 112. Table 8 is an example of how a part of the device profile data may be arranged within status DB 112.

TABLE 8

```
"FlowGenerator": {
  "IdentificationProfile": {
    "Product": {
      "UniversalIdentifier": "6a7a2e7e-5d9d-4c87-b45e-faa3563f21a8",
      "SerialNumber": "23140305348",
      "SerialNumberVerificationCode": "371",
      "ProductCode": "82001",
      "ProductName": "New Product",
      "ProductGeographicIdentifier": "AMR",
      "TimeZoneOffset": "-05:00"
    },
    "Hardware": {
      "HardwareIdentifier": "(90)R445-1003(91)3.0(21)706200143",
      "HardwareSerialNumber": "709011143",
      "HardwarePartIdentifier": "R111-1003",
      "HardwareVersionIdentifier": "3.0"
    },
    "Software": {
      "BootloaderIdentifier": "SW03901.00.3.0.0.48255",
      "ApplicationIdentifier": "SW03900.01.4.0.0.49820",
      "ConfigurationIdentifier": "CF03900.01.02.00.49820",
      "PlatformIdentifier": 33,
      "VariantIdentifier": 21,
      "ProfileVariationIdentifier": "71abc734-2133-49ae-878d-e49d075d0110",
      "DataVersionIdentifier": 1,
      "DataModelVersionIdentifier": "2.2.0.49383"
    }
  }
}
```

Here, the UniversalIdentifier may be the identifier that is the device identification data transmitted from the patient device. This is used to find all records (e.g., all "IdentificationProfiles") within the status DB 112 that are associated with that UniversalIdentifier. The above example from Table 8 shows a flow generator component with the "hardware" versioning information along with the currently installed "software" versions for that component that are present on the patient device associated with the indicated identifier. Additional records may also be included within the status DB 112 for different components of that device. For example, a Bluetooth module, a cellular module, a humidifier module, and the like may each have separate entries. Each of these components will also be associated with a universal identifier entry—"'UniversalIdentifier': '6a7a2e7e-5d9d-4c87-b45e-faa3563f21a8'" to thus allow looking up all components of a given patient device. In certain examples, the universal identifier is the same for all components within a device. In certain examples, the universal identifier is different for some components within (or coupled to) the same patient device.

At 352, the versioning information from the identification profiles of the various components is then processed, via rule manager module 108, against the rules that are stored on the MMS system 106 to determine if there are any available upgrade packages for components of this patient device. If there are no available upgrades, then the process ends and the MMS system 106 may simply respond to the request with "none" (or a similar message that no upgrades are available at this time).

If there is one or more available upgrade package(s), then those are transmitted to the patient device at 354. In the case of multiple upgrade packages, such packages may be applied sequentially via multiple different requests from the patient device to the MMS system 106. In other words, each sequential application of the rules by the rule manager module 108 (e.g., in response to different instances of the same device checking-in with the MMS system 106) may be used to determine a further upgrade that is to be applied to a given patient device. Thus, the ordering of the rules as they are processed by the rule manager module 108 may determine which upgrade package is to be applied (out of multiple possible upgrade packages). In certain examples, the way in which the MMS system 106 determines and then delivers upgrade packages to a device allows for the upgrades to be applied in a sequential and/or deterministic manner. For example, a device may fit multiple different preconditions (e.g., multiple upgrades need to be applied). The MMS system 106 may advantageously arbitrate such a request by determining which package to deliver based on the ordering of the segments within an upgrade specification. Thus, for example, rather than picking any precondition that is satisfied the MMS system may select the first one within the upgrade specification (e.g., assuming it is processed in order). This type of example approach allows the MMS system 106 to build, for example, a known safe chain of upgrades for requesting devices.

In any event, the upgrade package is transmitted to the patient device at 354. Then, at 356, the device status (e.g., transmitted at step 310 in FIG. 9A) is received by the MMS system 106.

At 358, the device status that is received at 356 is then stored. For example, if the patient device transmits version information for a given component, then that versioning information may be stored to status DB 112 (e.g., overwriting the previously stored versioning information for that component). Alternatively, if the upgrade is unsuccessful, then a record of that error may be stored and flagged for potential future follow-up.

In certain examples, the MMS system 106 may include one or more services that may each be executed or hosted on different computing devices. An example system that includes such services is shown in FIG. 10A. Services may include cloud service 400, request service 402, queue 404, and/or upgrade service 406. An example MMS system may include cloud service 400 that is for interfacing/communicating with patient devices 102. In certain examples, cloud service 400 may be hosted in a cloud-computing environment (e.g., Amazon AWS, Microsoft Azure, etc.) to provide high availability uptime and services that are geo-located for reduced latency. Each or any of the services discussed herein may be hosted within a separate virtualized container or instance within a cloud-based computer system. In certain examples, some services may be hosted outside of a cloud-based implementation and communicate with other services that are within a cloud-based implementation. In certain examples, each or any services may be hosted on its own computing node, some or any of which may be within a cloud-based systems and other outside. A computing node may include separate physical computer hardware and/or a separate virtualized container or instance.

Cloud service 400 may communicate with a separately provided request service 402 that is used to manage and create requests. In certain examples, requests are used to encapsulate upgrade packages (e.g. a request that a given device apply an upgrade package). Requests that have been generated may be stored in pending requests 114. In certain examples, request may also include requests to update or change configuration or other settings of a given patient device and/or a component thereof. The request service 402 may interface with queue 404 that is used to store pending requests (e.g., those that have yet to be sent to a patient device and/or have yet to be completed by a patient device). The request service 402 may also communicate with upgrade service 406 that is used to determine if any software or firmware upgrades are available for a given request (or to generate a request if an upgrade is available as is described in FIG. 10B).

Turning to FIG. 10A, an example of retrieval of a brokered (or pending) request is shown in accordance with certain examples. In FIGS. 10A-10C, distributed services (e.g., 400, 402, 404, and 406) are provided on separate computing resources and each provide different functionality. In certain examples, each or any of these services may be provided on a cloud-computing environment. Collectively, as discussed above, such services may be provided within the overall MMS system 106.

At 410, patient device 102 transmits identification data for the patient device to cloud service 400. This may be, for example, a cellularModuleUniversalIdentifier or other unique identifier that is used to uniquely identify the patient device 102. In certain examples, a MAC address may be used if the request from the patient device is sent via a network interface card of the patient device as opposed to a cellular modem.

At 412, the cloud service 400 issues a request to the request service 402 to obtain the current request that is associated with the transmitted identification data. In other words, this determines if there any current requests that are associated with the provided ID. This causes the request service 402 to access queue 404 at 414 to find the current request.

The request in the queue 404 is then returned as a brokered request at 416 to the request service 402, which then returns it to cloud service 400 at 418. The brokered request is then returned to the patient device 102 at 420. With this type of architecture, the functionality of the request and upgrade services may be encapsulated by the cloud service (at least from the perspective of any patient device that is checking in).

An example of data (a "BrokerItem") that may be included as part of a brokered request that is returned to patient device 102 is the broker item included in table 5 shown above. Another example is shown below in Table 9 and relates to a brokered request for an upgrade data package (a firmware upgrade in this case).

TABLE 9

```
"BrokerItem" : {
"ResponseCallbackUri " : "/v1/cloud/requests/item/ {uuid-r1-2}/status",
"RequestType": "FirmwareChange",
"RequestContent": {
"FirmwareChange": {
    "FirmwareChangeComponent": "FlowGenerator",
    "FirmwareFileUrl": https://{host}:{port}/uri",
    "FirmwareFileSize": {file size},
    "FirmwareFileHash256" : "{file hash}"
    }
}}
```

Another example is shown in Table 10 below and relates to a setting profiles request that may be included in a brokered request.

TABLE 10

```
"BrokerItem" : {
"ResponseCallbackUri" : "/v1/cloud/requests/item/ {uuid-r1-3}/status",
"RequestType": "SettingProfiles",
"RequestContent": {
  "SettingProfiles: {
   "Attributes": {
       "Source": "CLOUD",
       "TransactionIdentifier": 1234
     }
   "ActiveProfiles": {//Optional, if given will change active therapy mode
```

TABLE 10-continued

```
        "TherapyProfile": "AutoSet1Profile"
    }
    "TherapyProfiles" {//Optional, If given, will contain one or more
                      //complete therapy profiles
        "AutoSet1Profile": {
            "ThereapyMode": "Auto1"
            "StartPressure": 6.0,
            "MinPressure": 6.0,
            "MaxPressure": 18.0
    }
        "FeatureProfiles": {//Optional, will contain one or more complete profiles
            "EprFeature": {
                "EprEnablePatientAccess": "On",
                "EprEnable": "On",
                "EprType": "FullTime",
                "EprPressure": 3.0
                }
            }
        }
}}
```

Thus, profiles for settings for a patient device may be delivered via brokered requests.

In certain example embodiments, a brokered request that is delivered to a patient device may include one or more brokered items. In such an instance, individual brokered items within the overall request may be separately (and sequentially) delivered to the patient device. In other words, the patient device would process one BrokerItem before requesting the next BrokerItem. For example, each of the BrokerItems from Tables 5, 9, and 10 may be included into a single brokered request for a given patient device. Each BrokerItem may be delivered to a patient device in accordance with the embodiments discussed herein. In certain examples, each request may only include a single BrokerItem and multiple requests may be generated for a given patient device.

In certain example embodiments, upon reception of a brokered request, each, any or the BrokerItem within a corresponding request may be parsed and appropriate action may be taken by the patient device 102. For example, file(s) indicated in the BrokerItem may then be downloaded. In certain example embodiments, the patient device 102 may provide a report to the cloud service 400 that the file has been successfully downloaded. This status may then be appended or incorporated into the request that is currently pending for the given patient device (e.g., the request that is stored in queue 404). Once the file is downloaded it may then be applied to the patient device 102. In certain examples, the patient device 102 may then restart and a device status message may be transmitted to the cloud service that the upgrade component is now on the upgrade version (e.g., the upgrade version number may be specified). In certain examples, the status message may include information that the upgrade has been successfully applied to the patient device 102.

In certain examples, once a BrokerItem is transmitted to a device, it may be removed from queue 404 (e.g. the previously submitted Broker Request may be removed). In certain examples, successful application of a firmware upgrade may cause the BrokerItem associated with that request to be removed. If there are no pending BrokerItems, then the brokered request(s) in the queue 404 may be cleared for that patient device 102.

In certain examples, if an error is thrown during the upgrade process on the patient device 102, then the nature of the error may be reported back through cloud service 400 and stored for future analysis.

Turning to FIG. 10B, an example of a brokered firmware upgrade request is provided. Here, at 500, identification data is transmitted from patient device 102 to cloud service 400. Cloud service 400 then requests, from request service 402 at 502, the current brokered request based on the provided identification data. The request service 402 queries the queue 404 to find the current request at 504.

However, in this example, there is no current request so an empty set is returned at 506. The request service 402, then submits a request to the upgrade service 406 to determine if there is a firmware, software, or other upgrade is available based on the provided identification data for the patient device 102. As discussed herein, this may include querying the status DB 112 to obtain profile data of the patient device associated with the provided identification data and/or using rule manager module 108 to determine what upgrades or modifications should be applied to the given patient device 102.

When a firmware (or other upgrade for software or the like) is available, the details of that upgrade are returned from the upgrade service 406 to the request service 402 at 510. Such details may be similar to those shown in, for example, Table 9. For example, the location of where the file(s) are located may be provided, hashes of those files, sizes, components of the patient device that the files are for, etc.

Figure 1A:
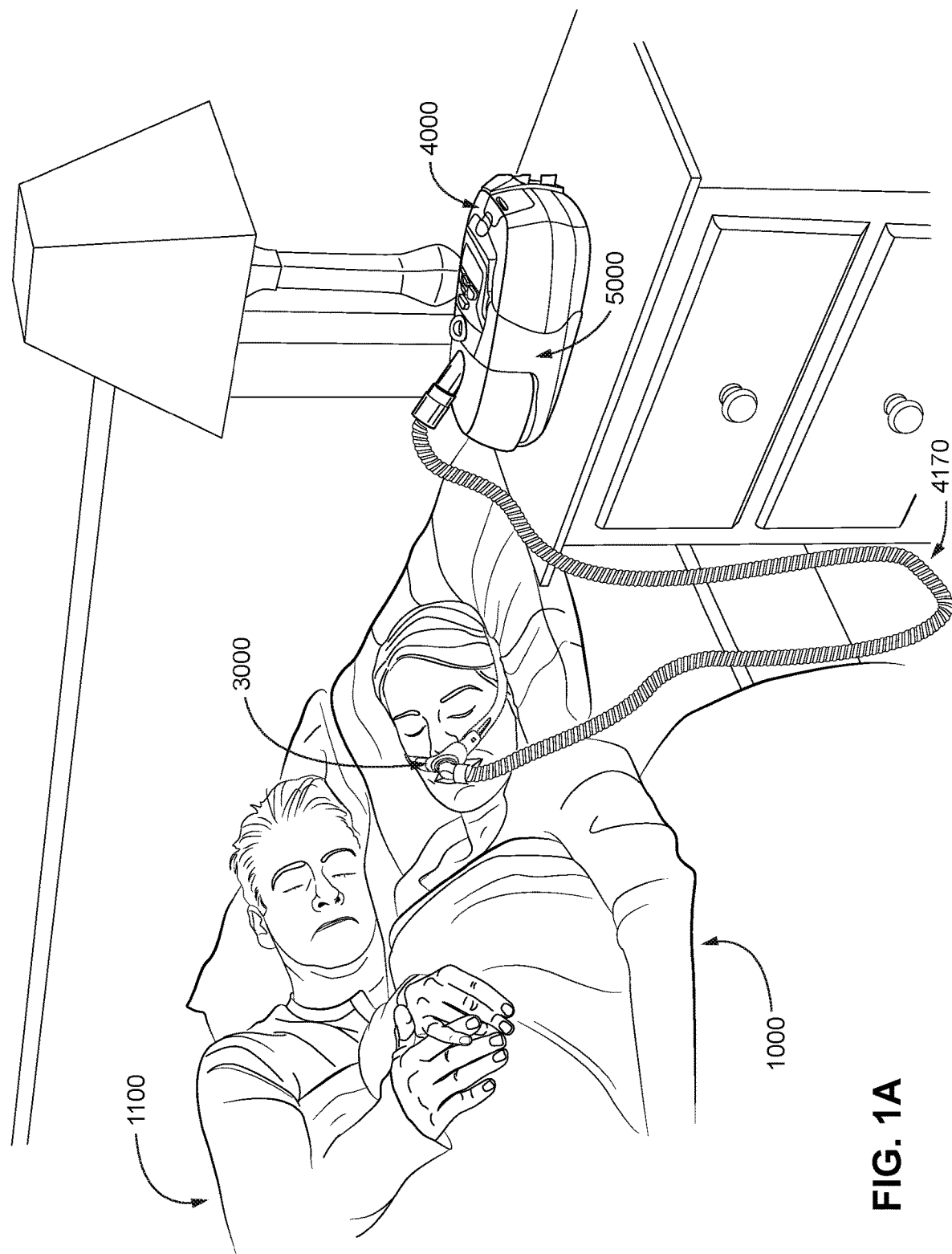
Figure 1B:
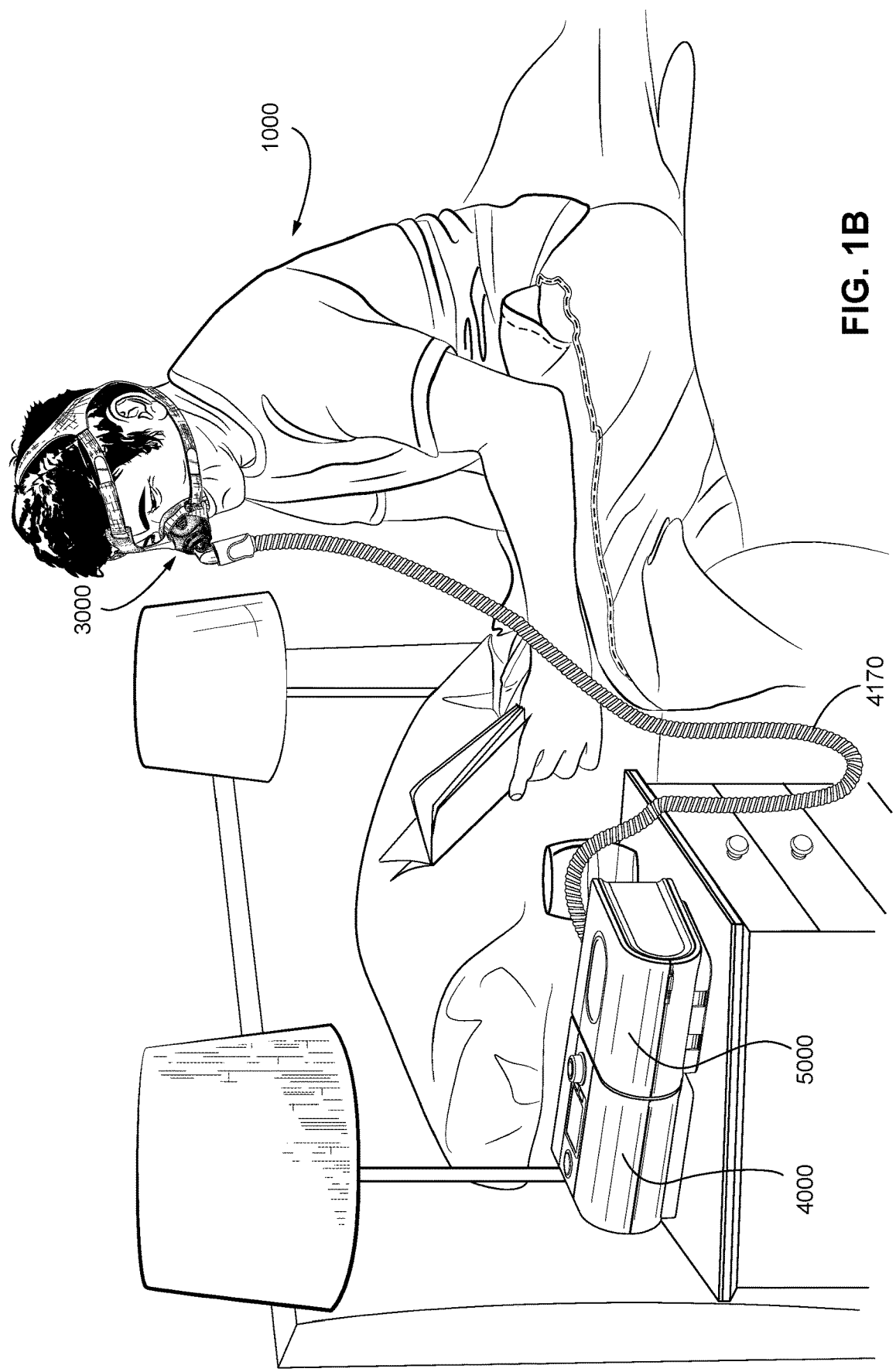
Figure 1C:
Figure 2A:
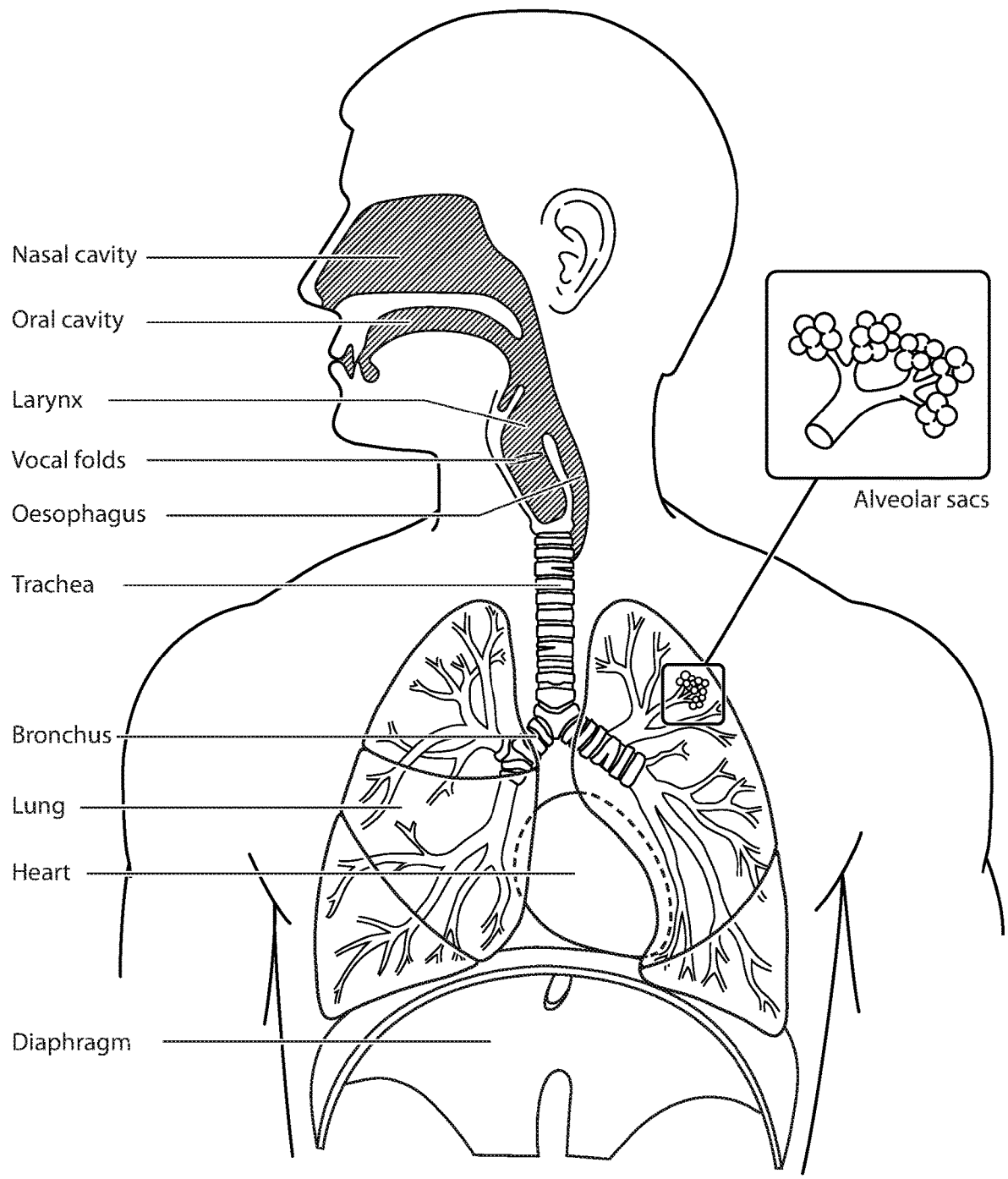
Figure 3A:
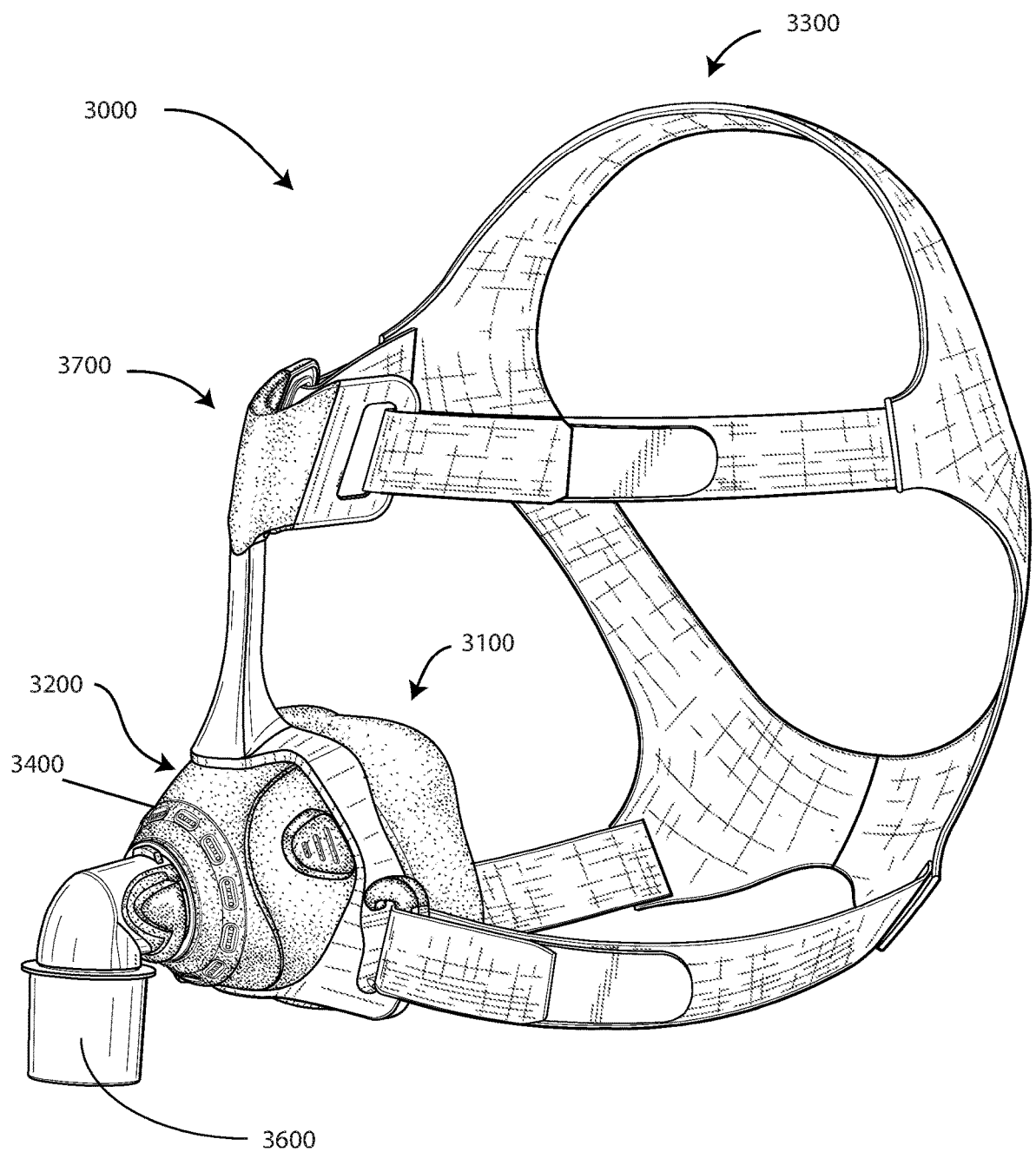

When the upgrade details are returned to the request service 402, the request service 402 may then create a brokered request based on those details at 512. This may include the creation of one or more BrokerItems for the brokered request as is shown in the above tables. The created request or items are then added to the queue 404 at 514 and then returned at 516 (e.g., similar to return of the request at 416 in FIG. 1A). This allows the system to keep track of the progress of requests (including upgrades) that need to be processed for each individual patient device. The created broker request (or BrokerItem) is then routed back to cloud service 400 at 518, which then communicates the brokered request back to the patient device 102 at 520. The processing thereafter may be similar as described in connection with FIG. 10A above where validation and application of the upgrade may occur.

FIG. 10C shows a signal diagram of what occurs when there is no broker request for patient device 102. At 600, the patient device 102 submits identification data to the cloud service 400. The cloud service then submits a request for a brokered request at 602 to the request service. The request service queries the queue 404 at 604. There is nothing in the queue 404, so nothing is returned at 606. The request service then submits a request at 608 to the upgrade service 406 to retrieve upgrade details. At 610 "none" or other similar response (e.g., that there are no applicable upgrades) may be returned from the upgrade service 406 indicating that there are no upgrades for the indicated device. A response of none is returned at 612 to the cloud service 400, which relays that response at 614 to the patient device 102.

5.10 Computing Device

FIG. 11 is a block diagram of an example computing device 1100 (which may also be referred to, for example, as a "computer device," "computer system," or "computing system") according to some embodiments. In some embodiments, the computing device 1100 includes one or more of the following: one or more processors 1102; one or more memory devices 1104; one or more network interface devices 1106; one or more display interfaces 1108; and one or more user input adapters 1110. Additionally, in some embodiments, the computing device 1100 is connected to or include display device(s) 1112. Additionally, in some embodiments, the computing device 1100 is connected to or includes one or more input devices 1114. In some embodiments, computing device 1100 may be connected to one or more external devices 1116. As will be explained below, these elements (e.g., the processors 1102, memory devices 1104, network interface devices 1106, display interfaces 1108, user input adapters 1110, display device 1112, input devices 1114, external devices 1116) are hardware devices (for example, electronic circuits or combinations of circuits) that are configured to perform various different functions for and/or in conjunction with the computing device 1100.

In some embodiments, each or any of the processors 1102 is or includes, for example, a single- or multi-core processor, a microprocessor (e.g., which may be referred to as a central processing unit or CPU), a digital signal processor (DSP), a microprocessor in association with a DSP core, an Application Specific Integrated Circuit (ASIC), a Field Programmable Gate Array (FPGA) circuit, or a system-on-a-chip (SOC) (e.g., an integrated circuit that includes, for example, a CPU, a GPU, and other hardware components such as memory and/or a memory controller (e.g., Northbridge), I/O controller (e.g., Southbridge), networking interfaces, and the like). In some embodiments, each or any of the processors 1102 uses an instruction set architecture such as x86 or Advanced RISC Machine (ARM). In some embodiments, each or any of the processors 1102 is or includes, for example, a graphical processing unit (GPU), which may be an electronic circuit designed to generate images and the like.

In some embodiments, each or any of the memory devices 1104 is or includes a random access memory (RAM) (such as a Dynamic RAM (DRAM) or Static RAM (SRAM)), a flash memory (based on, e.g., NAND or NOR technology), a hard disk, a magneto-optical medium, an optical medium, cache memory, a register (e.g., that holds instructions that may be executed by one or more of the processors 1102), or other type of device that performs the volatile or non-volatile storage of data and/or instructions (e.g., software that is executed on or by processors 1102). In some embodiments, each or any of the memory devices 1104 is removable from the computing device 1100 (such as a USB flash drive, a floppy disk, a Compact disc (CD), and the like). Memory devices 1104 are an example of non-transitory computer-readable storage. As used herein, the term "non-transitory computer-readable storage medium" includes a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVD, or Blu-Ray Disc, or other type of device for non-transitory electronic data storage. The term "non-transitory computer-readable storage medium" does not include a transitory, propagating electromagnetic signal.

In some embodiments, each or any of the network interface devices 1106 includes one or more circuits (such as a baseband processor and/or a wired or wireless transceiver), and implements layer one, layer two, and/or higher layers for one or more wired communications technologies (such as Ethernet (IEEE 802.3)) and/or wireless communications technologies (such as Bluetooth, WiFi (IEEE 802.11), GSM, CDMA2000, UMTS, LTE, LTE-Advanced (LTE-A), and/or other short-range, mid-range, and/or long-range wireless communications technologies). Transceivers may comprise circuitry for a transmitter and a receiver. The transmitter and receiver may share a common housing and may share some or all of the circuitry in the housing to perform transmission and reception. In some embodiments, the transmitter and receiver of a transceiver may not share any common circuitry and/or may be in the same or separate housings.

In some embodiments, each or any of the display interfaces 1108 is or includes one or more circuits that receive data from the processors 1102, generate (e.g., via a discrete GPU, an integrated GPU, a CPU executing graphical processing, or the like) corresponding image data based on the received data, and/or output (e.g., a High-Definition Multimedia Interface (HDMI), a DisplayPort Interface, a Video Graphics Array (VGA) interface, a Digital Video Interface (DVI), or the like), the generated image data to the display device 1112, which displays the image data. Alternatively or additionally, in some embodiments, each or any of the display interfaces 1108 is or includes, for example, a video card, video adapter, or graphics processing unit (GPU). In other words, the each or any of the display interfaces 1108 may include a processor therein that is used to generate image data. The generation or such images may occur in conjunction with processing performed by one or more of the processors 1102.

In some embodiments, each or any of the user input adapters 1110 is or includes one or more circuits that receive and process user input data from one or more user input devices 1114 that are included in, attached to, or otherwise in communication with the computing device 1100, and that output data based on the received input data to the processors 1102. Alternatively or additionally, in some embodiments each or any of the user input adapters 1110 is or includes, for example, a PS/2 interface, a USB interface, a touchscreen controller, or the like; and/or the user input adapters 1110 facilitates input from user input devices 1114.

In some embodiments, the display device 1112 may be a Liquid Crystal Display (LCD) display, Light Emitting Diode (LED) display, or other type of display device. In embodiments where the display device 1112 is a component of the computing device 1100 (e.g., the computing device and the display device are included in a unified housing), the display device 1112 may be a touchscreen display or non-touchscreen display. In embodiments where the display device 1112 is connected to the computing device 1100 (e.g., is external to the computing device 1100 and communicates with the computing device 1100 via a wire and/or via wireless communication technology), the display device 1112 is, for example, an external monitor, projector, television, display screen, etc . . . .

In some embodiments, each or any of the input devices 1114 is or includes machinery and/or electronics that generates a signal that is provided to the user input adapter(s) 1110 in response to physical phenomenon. Examples of inputs devices 1114 include, for example, a keyboard, a mouse, a trackpad, a touchscreen, a button, a joystick, a sensor (e.g., an acceleration sensor, a gyro sensor, a temperature sensor, a pressure sensor (e.g., that measures pressure of a gas), a flow sensor (e.g., the measures a rate of gas or liquid flow), and the like), a microphone. In some examples, one or more input devices 1114 generate signals that are provided in response to a user providing an input— for example, by pressing a button, speaking a voice command, or the like. In other examples, one or more input devices generate signals based on sensed physical quantities (e.g., such as force, pressure, temperature, etc.). In some embodiments, each or any of the input devices 1114 is a component of the computing device (for example, a button is provide on a housing that includes the processors 1102, memory devices 1104, network interface devices 1106, display interfaces 1108, user input adapters 1110, and the like).

In some embodiments, each or any of the external device(s) 1116 may include other computing devices (e.g., other instances of computing device 1100) that communicate with computing device 1100. Examples may include a server computer, a client computer system, a mobile computing device, a cloud-based computer system, a computing node, an Internet of Things (IoT) device, a flow generator, etc. that all may communicate with computing device 1100. In general, external devices(s) 1116 may include devices that communicate (e.g., electronically) with computing device 1100. As an example, computing device 1100 may be mobile device communicates with a flow generator or a patient interface device or mask (e.g., examples of external device 1116). Conversely, computing device 1100 may be a flow generator that communicates with server or cloud-based computer system, which are examples of external devices 1116, that provides data and/or software updates to the flow generator.

In various embodiments, the computing device 1100 includes one, or two, or three, four, or more of each or any of the above-mentioned elements (e.g., the processor(s) 1102, memory device(s) 1104, network interface device(s) 1106, display interface(s) 1108, user input adapter(s) 1110, display device(s) 1112, input device(s) 1114). Alternatively or additionally, in some embodiments, the computing device 1100 includes one or more of: a processing system that includes the processors 1102; a memory or storage system that includes the memory devices 1104; and a network interface system that includes the network interface devices 1106.

The computing device 1100 may be arranged, in various embodiments, in many different ways. As just one example, the computing device 1100 may be arranged such that the processors 1102 include: a multi (or single)-core processor; a first network interface device (which implements, for example, WiFi, Bluetooth, NFC, etc.); a second network interface device that implements one or more cellular communication technologies (e.g., 3G, 4G LTE, CDMA, etc.); memory or storage devices (e.g., RAM, flash memory, or a hard disk). The processor, the first network interface device, the second network interface device, and the memory devices may be integrated as part of the same SOC (e.g., one integrated circuit chip). As another example, the computing device 1100 may be arranged such that: the processors 1102 include two, three, four, five, or more multi-core processors; the network interface devices 1106 include a first network interface device that implements Ethernet and a second network interface device that implements WiFi and/or Bluetooth; and the memory devices 1104 include a RAM and a flash memory or hard disk. As another example, the computing device 5100 may include a SoC with one or processors 5102, plural network interface devices 5106 (e.g., one that uses communicates via a Cellular connection and one that communicates via a Bluetooth connection), memory devices 5104 that include system memory and memory for application programs and other software, a display interface 5108 that is configured to output a video signal, a display device 5112 that is integrated to a housing and layered with a touch screen input device 5114, and multiple input device 5114 such as one or more buttons and/or and one or more sensors.

As previously noted, whenever it is described in this document that a software module or software process performs any action, the action is in actuality performed by underlying hardware elements according to the instructions that comprise the software module. Consistent with the foregoing, in various embodiments, each or any combination of cloud service 400, request service 402, queue 404, upgrade service 406, MMS system 106, rule manager module 108, rules 110, status database 112, upgrade packages 116, and pending requests 114, each of which will be referred to individually for clarity as a "component" for the remainder of this paragraph, are implemented using an example of the computing device 1100 of FIG. 5. In such embodiments, the following applies for each component: (a) the elements of the 1100 computing device 1100 shown in FIG. 11 (i.e., the one or more processors 1102, one or more memory devices 1104, one or more network interface devices 1106, one or more display interfaces 1108, and one or more user input adapters 1110), or appropriate combinations or subsets of the foregoing, with or without the one or more display devices 1112, one or more input devices 1114, and/or external devices 1116) are configured to, adapted to, and/or programmed to implement each or any combination of the actions, activities, or features described herein as performed by the component and/or by any software modules described herein as included within the component; (b) alternatively or additionally, to the extent it is described herein that one or more software modules exist within the component, in some embodiments, such software modules (as well as any data described herein as handled and/or used by the software modules) are stored in the memory devices 1104 (e.g., in various embodiments, in a volatile memory device such as a RAM or an instruction register and/or in a non-volatile memory device such as a flash memory or hard disk) and all actions described herein as performed by the software modules are performed by the processors 1102 in conjunction with, as appropriate, the other elements in and/or connected to the computing device 1100 (e.g., the network interface devices 1106, display interfaces 1108, user input adapters 1110, display device(s) 1112, input device(s) 1114, and/or external device(s) 1116); (c) alternatively or additionally, to the extent it is described herein that the component processes and/or otherwise handles data, in some embodiments, such data is stored in the memory devices 1104 (e.g., in some embodiments, in a volatile memory device such as a RAM and/or in a non-volatile memory device such as a flash memory or hard disk) and/or is processed/handled by the processors 1102 in conjunction, as appropriate, the other elements in and/or connected to the computing device 1100 (e.g., the network interface devices 1106, display interfaces 1108, user input adapters 1110, display device 1112, input device(s) 1114, and/or external device(s) 1116); (d) alternatively or additionally, in some embodiments, the memory devices 1102 store instructions that, when executed by the processors 1102, cause the processors 1102 to perform, in conjunction with, as appropriate, the other elements in and/or connected to the computing device 1100 (e.g., the memory devices 1104, network interface devices 1106, display interfaces 1108, user input adapters 1110, display device(s) 1112, input device(s) 1114, and/or external device(s) 1116), each or any combination of actions described herein as performed by the component and/or by any software modules described herein as included within the component.

The hardware configurations shown in FIG. 11 and described above are provided as examples, and the subject matter described herein may be utilized in conjunction with a variety of different hardware architectures and elements. For example: in many of the Figures in this document, individual functional/action blocks are shown; in various embodiments, the functions of those blocks may be implemented using (a) individual hardware circuits, (b) using an application specific integrated circuit (ASIC) specifically configured to perform the described functions/actions, (c) using one or more digital signal processors (DSPs) specifically configured to perform the described functions/actions, (d) using the hardware configuration described above with reference to FIG. 11, (e) via other hardware arrangements, architectures, and configurations, and/or via combinations of the technology described in (a) through (e).

5.11 Glossary

For the purposes of the present technology disclosure, in certain forms of the present technology, one or more of the following definitions may apply. In other forms of the present technology, alternative definitions may apply.

5.11.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Patient: A person, whether or not they are suffering from a respiratory condition.

Respiratory Pressure Therapy (RPT): The application of a supply of air to an entrance to the airways at a treatment pressure that is typically positive with respect to atmosphere.

5.12 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps 1in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A system for managing updates provided to patient respiratory device, the system comprising:
    a patient respiratory device that includes a first memory configured to store firmware and/or software, a transceiver, and at least one hardware processor, the patient respiratory device comprising instructions that, when executed by the at least one hardware processor of the patient respiratory device, cause the at least one hardware processor of the patient respiratory device to perform first operations comprising:
        determining whether an update process should be performed, and
        based on determination that the update process should be performed, generating and transmitting an update check message that includes identification data for the patient respiratory device;
    an update system that includes a second memory and at least one hardware processor, update system comprising instructions stored to the second memory that, when executed by the at least one hardware processor of the update system, cause the at least one hardware processor of the update system to perform second operations comprising:
        storing a status database that includes records for a plurality of different patient respiratory devices, where each of the records includes versioning data identifying firmware and/or software installed on a respective one of the plurality of different patient respiratory devices,
        receiving and processing the update check message to retrieve, from the status database and based on the identification data of the patient respiratory device that is included in the update check message, device profile data of the patient respiratory device,
        based on the device profile data of the patient respiratory device, determining which of multiple possible upgrade packages is to be applied to the patient respiratory device,
        generating, based on which upgrade package(s) have been determined, an upgrade message that includes data for what upgrade to apply to the software and/or firmware of the patient respiratory device, and
        transmitting the upgrade message to the patient respiratory device; and
    the first operations further comprise:
        receiving the upgrade message, and
        executing, based on contents of the upgrade message, a upgrade process to apply the firmware and/or software to the patient respiratory device.

2. The system of claim 1, wherein the first operations further comprise:
    downloading the upgrade package based on the data specified in the upgrade message, wherein the upgrade that is applied is further based on the downloaded upgrade package.

3. The system of claim 1, wherein the first operations further comprise:
    communicating, after the upgrade is applied, a status update message to the update system, wherein the status update message includes versioning information of software and/or firmware of the applied upgrade.

4. The system of claim 1, wherein the second operations further comprise:
    storing a rules database that includes a plurality of records that each correspond to a different upgrade rule,
    wherein determining which of multiple possible upgrade packages is to be applied to the patient device includes selecting the upgrade rule to apply based on the device profile data, wherein the upgrade rule includes data that indicates a corresponding upgrade package to be applied.

5. The system of claim 4, wherein each of the plurality of records of the rules database includes at least one precondition,
    wherein selection of the upgrade rule includes matching the at least one precondition of the upgrade rule to data of the device profile data of the patient respiratory device.

6. The system of claim 1, wherein the second operations further comprise:
    determining, based on the identification data for the patient respiratory device, whether there is a pending request for the patient respiratory device.

7. The system of claim 6, wherein the second operations further comprise:
    based on determination that there is no pending request for the patient respiratory device, generating, based on which one(s) of the multiple possible upgrade packages is to be applied to the patient respiratory device, a request and storing the request to a data structure.

8. The system of claim 1, wherein the identification data of the patient respiratory device includes a unique identifier that uniquely identifies the patient respiratory device from other patient respiratory devices.

9. The system of claim 8, wherein the unique identifier is associated with a transceiver that is included with the patient respiratory device.

10. The system of claim 1, wherein versioning information for the software or firmware of the patient respiratory device is not included in the update check message.

11. The system of claim 1, wherein the update system includes a first computing node and a second computing node that each perform different ones of the second operations.

12. The system of claim 1, wherein the second operations further comprise:
    determining which of multiple possible upgrade packages is to be applied to the patient respiratory device, parsing through a plurality of upgrade segments that are specified in an upgrade specification until a pre-condition of one of the upgrade segments is matched to the versioning data of the device profile data for the patient respiratory device.

13. A non-transitory computer readable medium storing computer executable instructions for use with a computer system includes a respiratory patient device, and an update system, the respiratory patient device including electronic memory storing firmware and/or software thereon that is used to control operation of the respiratory patient device, the computer executable instructions including instructions configured to cause the computer system to perform operations comprising:
    on the respiratory patient device, determining whether an update process should be performed;
    on the respiratory patient device, based on determination that the update process should be performed, generating and transmitting an update check message that includes identification data for the patient respiratory device;
    on the update system:
        storing a status database that includes records for a plurality of different patient respiratory devices, where each of the records includes versioning data identifying firmware and/or software installed on a respective one of the plurality of different patient respiratory devices,
        receiving and processing the update check message to retrieve, from the status database and based on the identification data of the patient respiratory device that is included in the update check message, device profile data of the patient respiratory device,
        based on the device profile data of the patient respiratory device, determining which of multiple possible upgrade packages is to be applied to the patient respiratory device,
        generating, based on which upgrade package(s) have been determined, an upgrade message that includes data for what upgrade to apply to the software and/or firmware of the patient respiratory device, and
        transmitting the upgrade message to the patient respiratory device;
    on the respiratory patient device, receiving the upgrade message; and
    on the respiratory patient device, executing, based on contents of the upgrade message, a upgrade process to apply the firmware and/or software to the patient respiratory device.

14. The non-transitory computer readable medium of claim 13, wherein the operations further comprise, downloading the upgrade package based on the data specified in the upgrade message, wherein the upgrade that is applied is further based on the downloaded upgrade package.

15. The non-transitory computer readable medium of claim 13, wherein the operations further comprise, communicating, after the upgrade is applied, a status update message to the update system, wherein the status update message includes versioning information of software and/or firmware of the applied upgrade.

16. The non-transitory computer readable medium of claim 13, wherein the operations further comprise:
    storing a rules database that includes a plurality of records that each correspond to a different upgrade rule,
    wherein determining which of multiple possible upgrade packages is to be applied to the patient device includes selecting the upgrade rule to apply based on the device profile data, wherein the upgrade rule includes data that indicates a corresponding upgrade package to be applied.

17. The non-transitory computer readable medium of claim 16, wherein each of the plurality of records of the rules database includes at least one precondition,
    wherein selection of the upgrade rule includes matching the at least one precondition of the upgrade rule to data of the device profile data of the patient respiratory device.

18. The non-transitory computer readable medium of claim 13, wherein the operations further comprise, determining, based on the identification data for the patient respiratory device, whether there is a pending request for the patient respiratory device.

19. A method for managing updates provided to patient respiratory devices, the method comprising:
    storing, to electronic data storage, a status database that includes records for a plurality of different patient respiratory devices, including at least a first patient respiratory device and a second patient respiratory device, where each of the records includes versioning data identifying firmware and/or software installed on a respective one of the plurality of different patient respiratory devices,
    receiving a first update check message that includes identification data for the first patient respiratory device;
    receiving a second update check message that includes identification data for the second patient respiratory device;
    processing the first update check message to retrieve, from the status database and based on the identification data of the first patient respiratory device that is included in the first update check message, device profile data of the first patient respiratory device;
    based on the device profile data of the first patient respiratory device, determining which of multiple possible upgrade packages is to be applied to the first patient respiratory device;
    generating, based on which upgrade package(s) have been determined, a first upgrade message that includes data for what upgrade to apply to the software and/or firmware of the first patient respiratory device;
    transmitting the first upgrade message to the first patient respiratory device;
    as a result of reception of the second update check message, retrieving an existing brokered request that specifies firmware and/or software to be upgraded on the second patient respiratory device;

generating, based on the existing brokered request, a second upgrade message that includes data for what upgrade to apply to the software and/or firmware of the second patient respiratory device; and transmitting the second upgrade message to the second patient respiratory device.

20. The method of claim 19, wherein once the second update check message is received, the generation of the second upgrade message is performed without relying on the status database or the determining which of multiple possible upgrade packages is to be applied to the second patient respiratory device.

* * * * *